US011719709B2

(12) United States Patent
Makkad et al.

(10) Patent No.: US 11,719,709 B2
(45) Date of Patent: Aug. 8, 2023

(54) WATER SOLUBLE POLYMER SURFACTANT FOR SYNTHESIS OF FUNCTIONALIZED POLYSTYRENE NANOBEADS TOWARDS DETECTION OF BILIRUBIN IN HUMAN SERUM

(71) Applicant: Council of Scientific & Industrial Research, New Delhi (IN)

(72) Inventors: Sarabjot Kaur Makkad, Pune (IN); Asha Syamakumari, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 585 days.

(21) Appl. No.: 16/850,900

(22) Filed: Apr. 16, 2020

(65) Prior Publication Data
US 2021/0255206 A1  Aug. 19, 2021

(30) Foreign Application Priority Data
Feb. 14, 2020  (IN) .............................. 202011006477

(51) Int. Cl.
*C08L 25/18* (2006.01)
*G01N 33/72* (2006.01)
(Continued)

(52) U.S. Cl.
CPC ............ *G01N 33/728* (2013.01); *C08L 25/18* (2013.01); *G01N 33/582* (2013.01); *C08L 25/06* (2013.01); *G01N 33/96* (2013.01)

(58) Field of Classification Search
CPC .......... C08F 12/08; C08F 12/14; C08F 12/22; C08F 12/24; C08F 112/08; C08F 112/24;
(Continued)

(56) References Cited

U.S. PATENT DOCUMENTS 5,804,405 A  9/1998 Ahifors
2014/0021136 A1* 1/2014 Qiu ........................ B01J 20/288
521/53
2015/0315348 A1* 11/2015 Cheng ........................ C08J 7/02
216/55

OTHER PUBLICATIONS

Du et al., "Highly Sensitive and Selective Sensing of Free Bilirubin Using Metal-Organic Frameworks-Based Energy Transfer Process", ACS Appl. Mater. Interfaces, 2017, 9, 30925-30932.
(Continued)

*Primary Examiner* — Robert C Boyle
(74) *Attorney, Agent, or Firm* — Blank Rome LLP

(57) ABSTRACT

The present invention provides a water soluble polymer surfactant (PS-DGlu) of formula I which is utilized for synthesis of functionalized polystyrene nanobead covalently incorporating (oligo) p-phenylenevinylene (OPV) nanosensor (PSG-OPV-n) which in turn is useful for the detection of bilirubin in human serum. The present invention further provides a process for the preparation of the water soluble polymer surfactant (PS-DGlu) of formula (I) and a mini emulsion polymerization process for the synthesis of PSG-OPV-n.

(Continued)

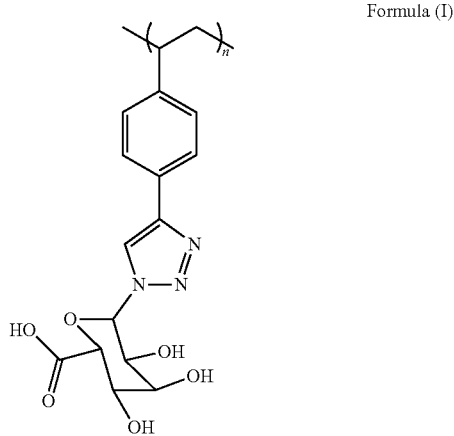

Formula (I)

wherein, n is 30-50.

The PSG-OPV-n nanosensor beads show selectivity towards detection of bilirubin in presence of interferences such as glucose, sucrose, metal ions, cholesterol, and biliverdin with limit of detection of 20 nM. Ultimately, the invention also provides a kit for visual detection of bilirubin in human serum.

14 Claims, 15 Drawing Sheets

(51) Int. Cl.
*G01N 33/58* (2006.01)
*C08L 25/06* (2006.01)
*G01N 33/96* (2006.01)

(58) Field of Classification Search
CPC .... C08F 112/16; C08F 212/24; C08F 212/16; C08F 212/08; C08F 112/14; C08F 212/14; C08F 212/22; C08F 112/22; C08F 12/16; C08F 8/30
See application file for complete search history.

(56) References Cited

OTHER PUBLICATIONS

Zhang et al.. Self-assemblies of amphiphilic homopolymers: synthesis, morphology studies and biomedical applications, Chem Commun., 2015, 51, 11541-11555.
Basu et al., "Invertible Amphiphilic Homopolymers", J.Am Chem. Soc., 2004, 126, 9890-9391.
Arumugam et al., Amphiphilic Homopolymer as a Reaction Medium in Water: Product Selectivity within Polymeric Nanopockets, J. Am. Chem. Soc., 2005, 127, 13200-13206.
Basu et al., "Hornopolymer Micelles in Heterogeneous Solvent Mixtures", J. Am. Chem. Soc. 2005, 127, 16794-16795.
Senthilkumar et al., "Self Assembly in Tailor-Made Polyfluorenes: Synergistic Effect of Porous Spherical Morphology and FRET for Visual Sensing of Bilirubin", ACS Publications, Macromolecules 2013, 46, 2159-2171.
Santhosh et al., "Selective and sensitive detection of free bilirubin in blood serum using human serum albumin stabilized gold nanoclusters as fluorometric and colorimetric probe", Biosensors and Bioelectronics 59, 2014, 370-376.
Ellairaja et al., "A green and facile approach for synthesizing imine to develop optical biosensor for wide range detection of bilirubin in human biofluids", Biosensors and Bioelectronics, 91, 2017, 82-88.
Makkad et al., "z-Conjugated Chromophore Incorporated Polystyrene Nanobeads asSingle Optical Agent for Three-Channel Fluorescent Probe in Bioimaging Application", ACS Biomaterials, Sci. Eng., 2017, 3, 1788-1798.
Senthilkumar et al. "Selective and Sensitive Sensing of Free Bilirubin in Human Serum Using Water-Soluble Polyfluorene as Fluorescent Probe", Macromolecules 2015, 48, 3449-3461.

* cited by examiner

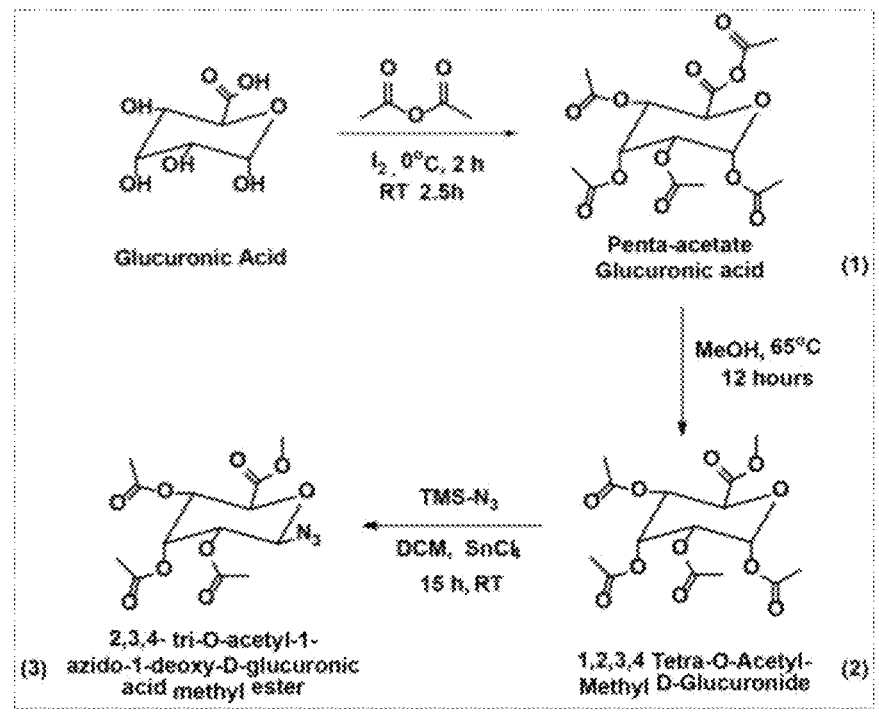
A
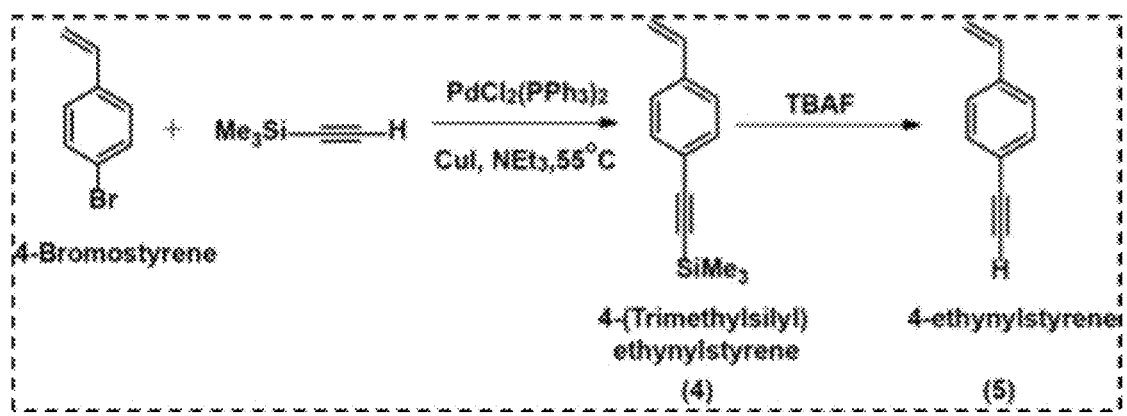
B
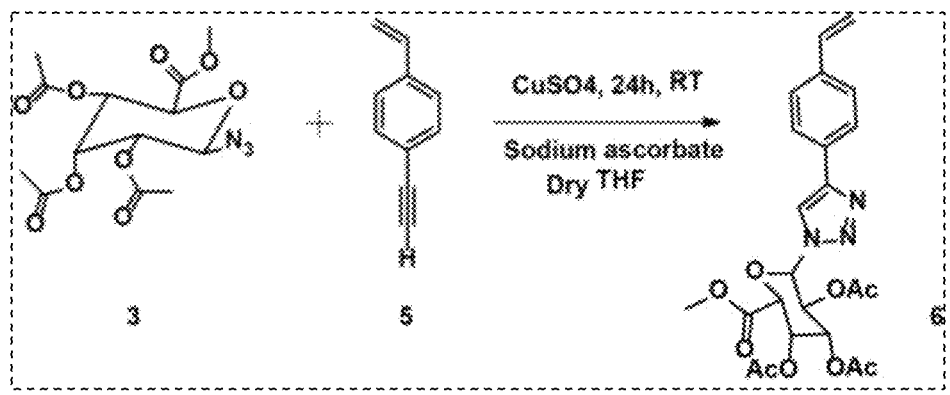
C
FIG. 21: Schemes A-C (13/15)

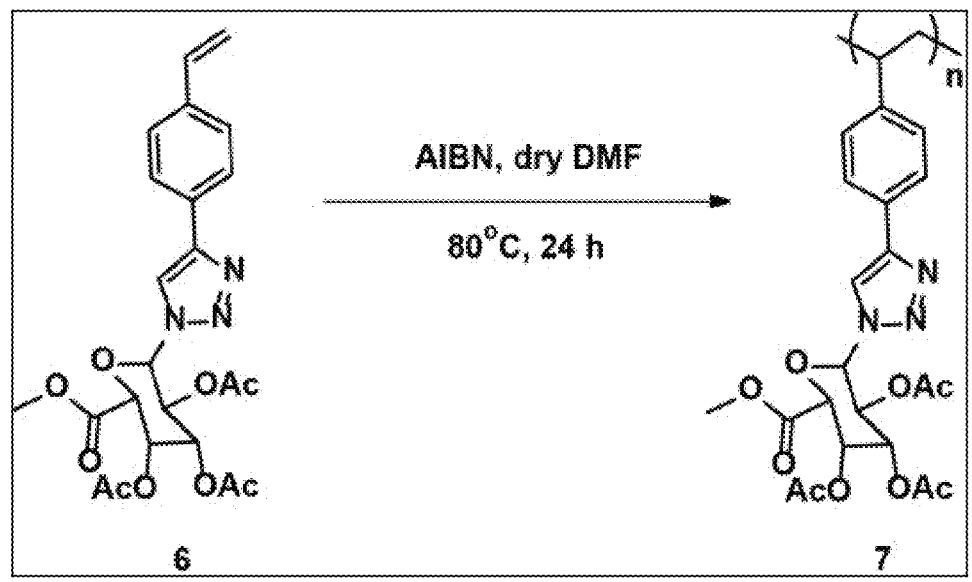
D
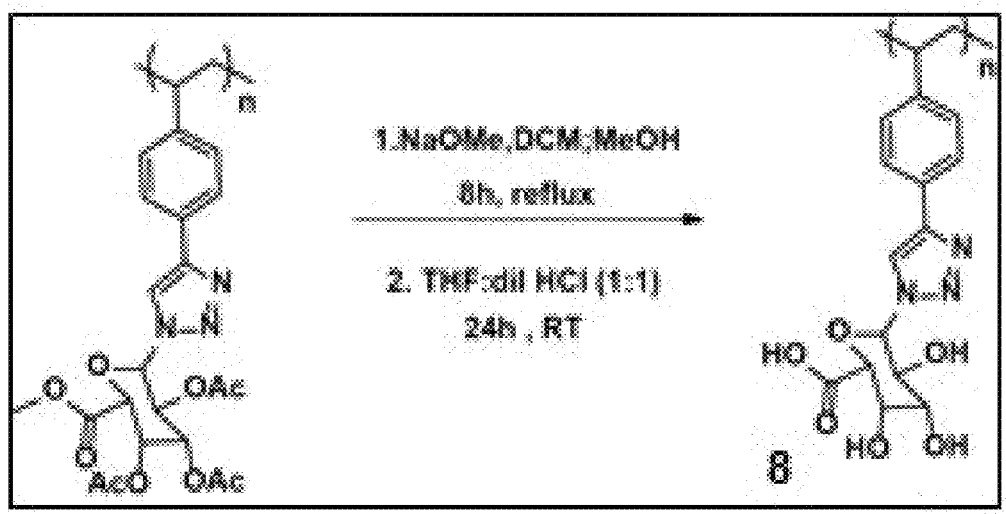
E
FIG. 22: Schemes D-E

WATER SOLUBLE POLYMER SURFACTANT FOR SYNTHESIS OF FUNCTIONALIZED POLYSTYRENE NANOBEADS TOWARDS DETECTION OF BILIRUBIN IN HUMAN SERUM

CROSS REFERENCE TO RELATED APPLICATION

This application claims priority to Indian Application No. 202011006477, filed on Feb. 14, 2020, the entire contents of which is incorporated by reference herein.

FIELD OF THE INVENTION

The present invention relates to a water soluble polymer surfactant (PS-DGlu) of formula I which is utilized for synthesis of functionalized polystyrene nanobead covalently incorporating (oligo) p-phenylenevinylene (OPV) nanosensor (PSG-OPV-n) which in turn is used for the detection of bilirubin in human serum. More particularly, the present invention relates to a process for synthesis of PS-DGlu and a mini-emulsion polymerization process utilizing PS-DGlu to obtain PSG-OPV-n. The developed PS based nanosensor (PSG-OPV-n) finds application in real time monitoring of free bilirubin in human serum with lower limit of detection of 20 nM.

BACKGROUND OF THE INVENTION

Amphiphilic polymers find applications in wide range of areas from materials to biology, such as drug delivery, catalysis, electronics, biosensing, etc. In this aspect, amphiphilic block copolymers for PS-b-poly(vinyl alcohol), PS-b-poly(acrylic acid), etc. where one block is hydrophilic while the other is hydrophobic have been extensively investigated. These amphiphilic block copolymers can exhibit broad range of self-assembled morphologies, which is driven by the mutual immiscibility of the constituent blocks with each other or in solvent. However, synthesis of such an amphiphilic copolymer is rather challenging mainly because, even if one block is synthesized in a controlled manner, the generation of a second block would be constrained due to incompatible solubility of these amphiphiles in common organic solvents.

Instead, the synthesis of amphiphilic homopolymers is more facile, demanding and controlled where 1:1 ratio of hydrophilic and hydrophobic unit could be exactly maintained along the long polymer chain (*Chem. Commun.* 2015, 51, 11541-11555). Introducing amphiphilicity at such small length scale would enable each monomer unit of polymer to behave as single surfactant moiety; thereby enhancing its surfactant property. However, unlike amphiphilic copolymers, the self-assembly of such homopolymer is usually driven by intra-molecular phase separation (*J. Am. Chem. Soc.* 2004, 126, 9890-9891). The group of Thayumanavan has reported an amphiphilic polystyrene homopolymer, which could be used as a reaction medium for photochemical reactions in water (*J. Am. Chem. Soc.* 2005, 127, 13200-13206) with superior selectivity compared to block copolymer micelles or small molecule surfactants (*J. Am. Chem. Soc.* 2004, 126, 9890-9891). The same group also demonstrated that the self-assembly in such amphiliphilic homopolymer could exhibit nanocontainer properties for separation as well as drug delivery application (*J. Am. Chem. Soc.* 2005, 127, 16794-16795).

Bilirubin is a yellow compound that occurs in the normal catabolic pathway that breaks down hemoglobin from erythrocytes undergoing normal or abnormal destruction within mononuclear phagocytes. Bilirubin gets metabolized in liver and finally is excreted from the body in the form of bile. Bilirubin is classified as indirect (free or unconjugated) and direct (conjugated). It is mostly present in conjugated form which is bound with human serum albumin making it water soluble. It is taken up by the liver and rendered water soluble by conjugation with glucuronic acid.

Bilirubin is measured as part of liver function tests including albumin, total protein, transaminase and alkaline phosphatase. Any disruption in normal metabolic pathways due to any reason including viral or bacterial infection causes excess breakdown of RBCs leading to excess production of free bilirubin in the body. Abnormal levels of total bilirubin (conjugated and unconjugated) detected in serum samples is an indicator for disturbed bilirubin metabolism. Free bilirubin is extremely fatal, and its excess accumulation above the normal level, i.e., <25 to >50 µmol/L, in human serum is directly related to jaundice, liver disorders, dysfunction of the common bile duct, gallstones, cancer of gallbladder, etc. Thus, determination of the precise amount of bilirubin in body fluid, especially in blood and serum is a crucial factor to diagnose liver disorders and jaundice.

Various common methods of determination of bilirubin include diazotization, enzymatic and spectroscopic methods. In diazotization, bilirubin is coupled with diazonium salt such as diazosulfanilic acid and the amount of the resulting colorant is measured in a spectrophotometer to estimate the bilirubin content in the sample.

In enzymatic method, the enzyme bilirubin oxidase is converted to biliverdin followed by measuring the absorbance. In spectrophotometric method, the maximum absorbance of bilirubin is measured at 437 nm.

Another method is to measure bilirubin on the basis of changes in absorbance of bilirubin by allowing an oxidizing agent to act on bilirubin in a sample of living body fluid to oxidize bilirubin. The method for measuring bilirubin, using such an oxidizing agent includes for example, a BOD method using bilirubin oxidaze (BOD) as an oxidizing agent, a chemical oxidation method using ferricyanide ions, copper ions, vanadate ions, etc. Other methods include, for example, a high performance liquid chromatography method, a film method using a mordant-coated film, etc.

Literature reports on the fluorometric detection of free bilirubin in human serum are also reported. Santhosh et al., Ellairaja et al., Du et al. reported protein labelled fluorescent biomolecules for monitoring of free bilirubin in serum. Metal-organic framework (MOF) based highly efficient bilirubin sensor was reported by Du et al., with faster response time, lower detection limit (picomolar) and wide range of analyte concentration. However, most of these sensors are accompanied by attenuation in their fluorescence intensity i.e., emission quenching on adding analyte.

Selective and sensitive detection of free bilirubin in blood serum using human serum albumin stabilized gold nanoclusters as fluorometric and colorimetric probe is disclosed in Biosens. Bioelectron, 2014, 59, 370-376. As per this publication, the fluorescence of the nanoclusters is strongly quenched by bilirubin and it provides "turn off" emission. On the contrary, the present invention is not an emission turn off; rather it is an emission color change i.e., the blue emission of OPV is changed to blue green emission, which is distinct to the naked eye.

Self-Assembly in tailor-made polyfluorenes: synergistic effect of porous spherical morphology and FRET for visual sensing of bilirubin (Macromolecules, 2013, 46, 2159-2171) disclosed two new fluorene based homo-(PDP-PF) and (PDPPF-co-Ph) copolymers with a bulky 3-pentadecylphenoxy (PDP) group appended hexyl chains at the 9,9' position using Suzuki coupling polymerization. However, for practical applications, a conjugated polymer-based biosensor is not so feasible due to the difficulties in the reproducible synthesis and scale up.

π-Conjugated Chromophore Incorporated Polystyrene Nanobeads as Single Optical Agent for Three-Channel Fluorescent Probe in Bioimaging Application (*ACS Biomater. Sci. Eng*, 2017, 3, 1788-1798) disclosed fluorescent polystyrene (PS) nanobeads in the size range ~70-120 nm incorporating perylenebisimide (PBI-PS) and/or oligo(p-phenylenevinylene) (OPV-PS) obtained using mini-emulsion polymerization technique. However, one of the limitation of this mini-emulsion polymerization technique is that higher amounts of SDS as small molecule based surfactant will be required.

U.S. Pat. No. 5,804,405 disclosed a method and kit for the selective determination of the total concentration of bilirubin ($B_t$), the concentration of conjugated bilirubin ($B_c$), the concentration of unconjugated bilirubin ($B_u$), the concentration of unbound bilirubin (b), the concentration of unbound, unconjugated bilirubin ($b_u$) using a unique combination of enzymatic and colorimetric methods in a single assay. Although this patent allows the separate estimation of bound and unbound bilirubin, the colorimetric analysis is usually a time consuming process unlike a quick fluorimetric based detection.

Glucuronic acid functionalized polyfluorene as a sensor for bilirubin (Macromolecules 2015, 48, 3449-3461) demonstrated the detection limit of 150 nM. Further, it demonstrated that polyfluorene sensor which was completely soluble in water and the complete access of sensor resulted in its quenching due to energy transfer to bilirubin giving faint green emission from bilirubin. However, due to poor quantum yield of bilirubin in water, intensity of that green emission in water was very weak.

All the above mentioned methods have demerits/limitations and so far none has been found to be satisfactory. In the diazo method the reagent is unstable which is effective only for about 5 days after the preparation and also ascorbic acid or hemoglobin present in the sample may interfere with the measurement values. The BOD method uses enzyme which inevitably increases measurement costs and the enzyme is effective only for 2 weeks after the preparation because the enzyme is difficult to be stabilized. The chemical oxidation method uses highly toxic metal ions which inevitably poses a waste water treatment/environmental pollution problem.

Thus, based on the limitations present in the prior art as discussed above, there is a need to develop fluorescent nanosensor with narrow size range suitable for bio-sensing application for quantifying free bilirubin in human serum using easy synthesis protocol and economical materials as compared to the current clinically practiced methods.

The present invention provides a water soluble polymer PS-DGlu as a surfactant for stabilizing mini-emulsion polymerization to obtain functionalized polystyrene nanobead covalently incorporating (oligo) p-phenylenevinylene (OPV) nanosensor (PSG-OPV-n), which are further used for the detection of bilirubin in human serum among a pool of other competitive interference, such as proteins, metal ions, cholesterol, sugars, biliverdin, etc. In the polymer surfactant PS-DGlu, glucuronic acid was chosen as the pendent with an aim to serve two main functions. It imparts water solubility to the PS-DGlu polymer, thereby enabling it to act as a surfactant in mini-emulsion polymerization. Second, it can provide interaction sites for bilirubin to enhance sensor-analyte synergy via hydrogen bonding. It may be the first report of PS homopolymer being applied as surfactant in mini-emulsion polymerization. Most of the reported polymeric surfactants are based on block copolymer design, which is synthetically more challenging compared to a homopolymer synthesis. The (oligo) p-phenylenevinylene was chosen as a sensing material because of its nice spectral overlap with bilirubin, thus favoring the energy transfer process. Overall, a PS based biocompatible polymeric bead based fluorimetric sensing and estimation protocol for bilirubin is highly desirable since the process would be fast and much more sensitive besides being easy to synthesize and scale up.

OBJECTIVES OF THE INVENTION

The main objective of the present invention is to visually detect bilirubin in human serum using polystyrene nanobead covalently incorporating (oligo) p-phenylenevinylene (OPV) nanosensor (PSG-OPV-n) beads with high quantum yield of chromophore in water and to provide a trigger free emission.

Another objective of the present invention is to provide a water soluble polymer surfactant (PS-DGlu) of formula (I) comprising hydrophobic polystyrene and hydrophilic glucuronic acid units joined together with a triazole moiety and a process for the preparation of same.

Yet another objective of the present invention is to provide glucuronic acid functionalized polystyrene nanobead covalently incorporating (oligo) p-phenylenevinylene (OPV) nanosensor (PSG-OPV-n) beads using a mini emulsion polymerization process using the water soluble surfactant (PS-DGlu) of formula (I).

Yet another objective of the present invention is to provide a process and a kit for the detection of bilirubin in human serum.

SUMMARY OF THE INVENTION

Accordingly, the present invention provides a water soluble polymer surfactant of formula (I) comprising a hydrophobic polystyrene and a hydrophilic glucuronic acid units joined together with a triazole moiety,

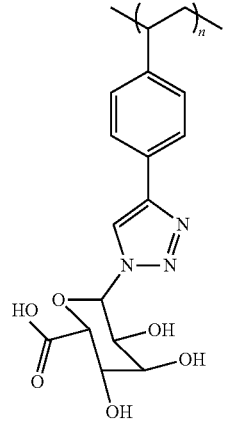

Formula (I)

wherein n is 30-50

In an embodiment, the present invention provides a process for preparation of the water soluble polymer surfactant of formula (I), comprising the steps of:

a) adding an iodine solution to a mixture of D-glucuronic acid and an acetic anhydride at a temperature in the range of 0° C. to –5° C. to obtain a reaction mixture; stirring the reaction mixture at a temperature in the range of 0° C. to –5° C. for a time period ranging from 2 to 3 hours followed by stirring at a temperature in the range of 25° C. to 30° C. for a time period ranging from 3 to 4 hours to obtain a penta-acetate glucuronic acid (1)

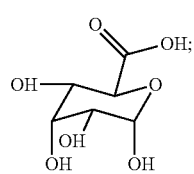

Glucuronic Acid

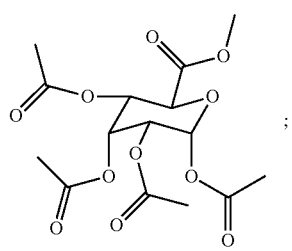

(1)

b) refluxing the penta-acetate glucuronic acid (1) as obtained in step (a) in dry methanol at a temperature in the range of 60° C. to 90° C. for a time period ranging from 12 to 26 hours to obtain 1, 2, 3, 4-Tetra-O-acetyl-methyl-β-D-glucuronide (2)

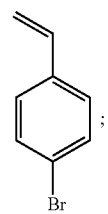

(2)

c) adding a TMS-azide and a tin (IV) chloride to the 1, 2, 3, 4-Tetra-O-Acetyl-methyl-β-D-Glucuronide (2) as obtained in step (b) in a solvent followed by stirring at a temperature in the range of 25° C. to 30° C. for a time period ranging from 15 to 20 hours to obtain 2, 3, 4-tri-O-acetyl-1-azido-1-deoxy-β-D-glucuronic acid methyl ester (3)

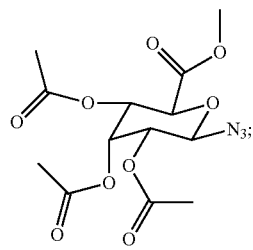

(3)

d) heating a reaction mixture of 4-bromostyrene, ethynyltrimethylsilane, copper(I) iodide and triethyl amine at a temperature in the range of 50 to 60° C. for a time period ranging from 5 to 15 minutes followed by adding bis(triphenylphosphine) palladium (II) dichloride followed by stirring at a temperature in the range of 50 to 60° C. for a time period ranging from 16 to 17 hours to obtain 4-(trimethylsilane)ethynylstyrene (4)

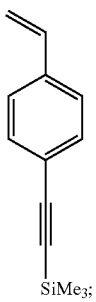

4-Bromostyrene (4)

e) adding a tetra-n-butyl ammonium fluoride to the 4-(Trimethylsilane)ethynylstyrene (4) as obtained in step (d) in a solvent to obtain a reaction mixture, followed by stirring the reaction mixture at a temperature in the range of 25 to 30° C. for a time period ranging from 1 to 2 hours to obtain 4-ethynylstyrene (5)

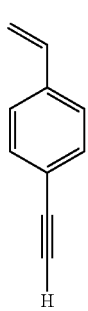

(5)

f) adding a copper sulfate and a sodium ascorbate in a water to the 4-ethynylstyrene (5) as obtained in step (e) and the 2, 3, 4-tri-O-acetyl-1-azido-1-deoxy-β-D-glucuronic acid methyl ester (3) as obtained in step (c) in a solvent to obtain a reaction mixture; stirring the reaction mixture at a temperature in the range of 25° C. to 30° C. for a time period ranging from 24 to 25 hours to obtain (2R, 3S, 4R, 5S, 6R)-2-(methoxycarbonyl)-6-(4-(4-vinylphenyl)-1H-1,2,3-triazol-1-yl)tetrahydro-2H-pyran-3,4,5-triyl triacetate (6)

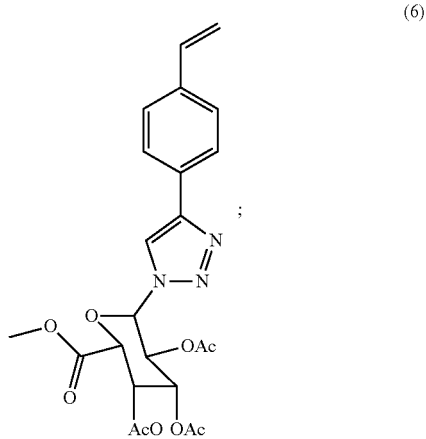 [SMILES: C=Cc1ccc(-c2cn(C3OC(C(=O)OC)C(OC(C)=O)C(OC(C)=O)C3OC(C)=O)nn2)cc1]

g) heating a mixture of (2R, 3S, 4R, 5S, 6R)-2-(methoxycarbonyl)-6-(4-(4-vinylphenyl)-1H-1,2,3-triazol-1-yl) tetrahydro-2H-pyran-3,4,5-triyl triacetate (6) as obtained in step (f), AIBN and a solvent at a temperature in the range of 80° C. to 90° C. for a time period ranging from 24 to 25 hours to obtain a protected polymer (7)

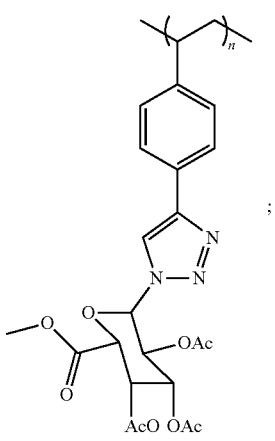

h) adding a sodium methoxide in a solvent into the protected polymer (7) as obtained in step (g) in a solvent, followed by stirring and refluxing for a time period ranging from 8 to 10 hours to obtain a polymer; and i) dissolving the polymer as obtained in step (h), in a solvent followed by adding hydrochloric acid and stirring at a temperature in the range of 25 to 30° C. for a time period ranging from 24 to 25 hours to obtain the water soluble polymer surfactant (PS-DGlu) of formula (I).

In an embodiment, the present invention provides the process for the preparation of water soluble polymer surfactant (PS-DGlu) of formula (I) in which the solvent is selected from the group consisting of methanol, dichloromethane, tetrahydrofuran, dimethyl formamide, water or a combination thereof.

In an embodiment, the present invention provides a mini-emulsion polymerization process using the glucuronic acid functionalized polystyrene (PS-DGlu) surfactant polymer, comprising the steps of:
a) preparing an organic phase comprising a styrene, a co-stabilizer and a polymerizable (oligo) p-phenylenevinylene (OPV) dye;
b) preparing an aqueous phase comprising an initiator and the glucuronic acid functionalized polystyrene (PS-DGlu) polymer in a water;
c) adding the organic phase as obtained in step (a) drop-wise to the aqueous phase as obtained in step (b) and pre-emulsifying at a temperature in the range of 21° C. to 25° C. followed by sonication under ice cooled condition to obtain a mini-emulsion;
d) polymerization of the mini-emulsion as obtained in step (c) at a temperature of 70° C. for 20 hours with a stirring at a speed of 750 rpm to obtain a polymerized mini-emulsion;
e) quenching the polymerized mini-emulsion as obtained in step (d) to obtain a latex; and
f) purifying the latex as obtained in step (e) to obtain a glucuronic acid functionalized polystyrene nanobead covalently incorporating (oligo) p-phenylenevinylene (OPV) nanosensor (PSG-OPV-n) bead.

In an embodiment, in the process of mini-emulsion, quenching is achieved by adding two drops of 1 wt % hydroquinone.

In an embodiment, in the process of mini-emulsion, the latex is purified by dialysis using 6 kD MW cut-off membrane for three days.

In an embodiment, in the process of mini-emulsion, the co-stabilizer is selected from the group consisting of hexadecane, cetyl alcohol, dodecyl methacrylate or stearyl methacrylate.

In an embodiment, in the process of mini-emulsion, the initiator is selected from the group consisting of 4,4'-Azobis (4-cyanovaleric acid) (ACVA), azobisisobutyronitrile (AIBN), potassium peroxydisulfate (KPS), lactoperoxidase (LPO) or benzoyl peroxide (BPO).

In an embodiment, w/w ratio of glucuronic acid functionalized polystyrene (PS-DGlu) to (oligo) p-phenylenevinylene (OPV) is 1-5:3 in the glucuronic acid functionalized polystyrene nanobead covalently incorporating (oligo) p-phenylenevinylene (OPV) nanosensor (PSG-OPV-n) nanobeads.

In an embodiment, size of the glucuronic acid functionalized polystyrene nanobead covalently incorporating (oligo) p-phenylenevinylene (OPV) nanosensor (PSG-OPV-n) nanobeads is in the range of 163 to 328 nm.

In another embodiment, the present invention provides a method of detection of bilirubin, comprising the steps of:
a) preparing a sample solution in a water or a buffer at pH=10 by the addition of NaOH;
b) titrating the glucuronic acid functionalized polystyrene nanobead covalently incorporating (oligo) p-phenylenevinylene (OPV) nanosensor (PSG-OPV-n) bead in a distilled water or a buffer with the sample solution of step (a); and c) determining by fluorimetry, a quenching of fluorescence intensity at 446 nm λmax, confirming the presence of bilirubin.

In yet another embodiment, the present invention provides a kit for the visual detection of bilirubin, comprising:
  a) a stock solution of the glucuronic acid functionalized polystyrene nanobead covalently incorporating (oligo) p-phenylenevinylene (OPV) nanosensor (PSG-OPV-n) bead;
  b) a graduated dropper;
  c) an analysis chamber; and
  d) an UV chamber.

In yet another embodiment, the present invention also provides a process for the visual detection of bilirubin in a sample by using the kit, comprising the steps of:
  a) adding a sample into the stock solution of the glucuronic acid functionalized polystyrene nanobead covalently incorporating (oligo) p-phenylenevinylene (OPV) nanosensor (PSG-OPV-N) bead with the help of a dropper to obtain a sample solution;
  b) pouring the sample solution of step (a) into an analysis chamber equipped with an UV chamber at the bottom; and
  c) detecting a change in blue emission of the sample solution of (b), confirming the presence of bilirubin.

In another embodiment, the change in blue emission of the sample solution is visually detected by turning into cyan indicates the presence of bilirubin in the sample.

BRIEF DESCRIPTION OF THE DRAWINGS

FIG. 21: Schemes A-C: Preparation of compounds (1) to (6).

FIG. 22: Schemes D-E: Preparation of compounds (7) & (8).

LIST OF ABBREVIATIONS

Figure 1:
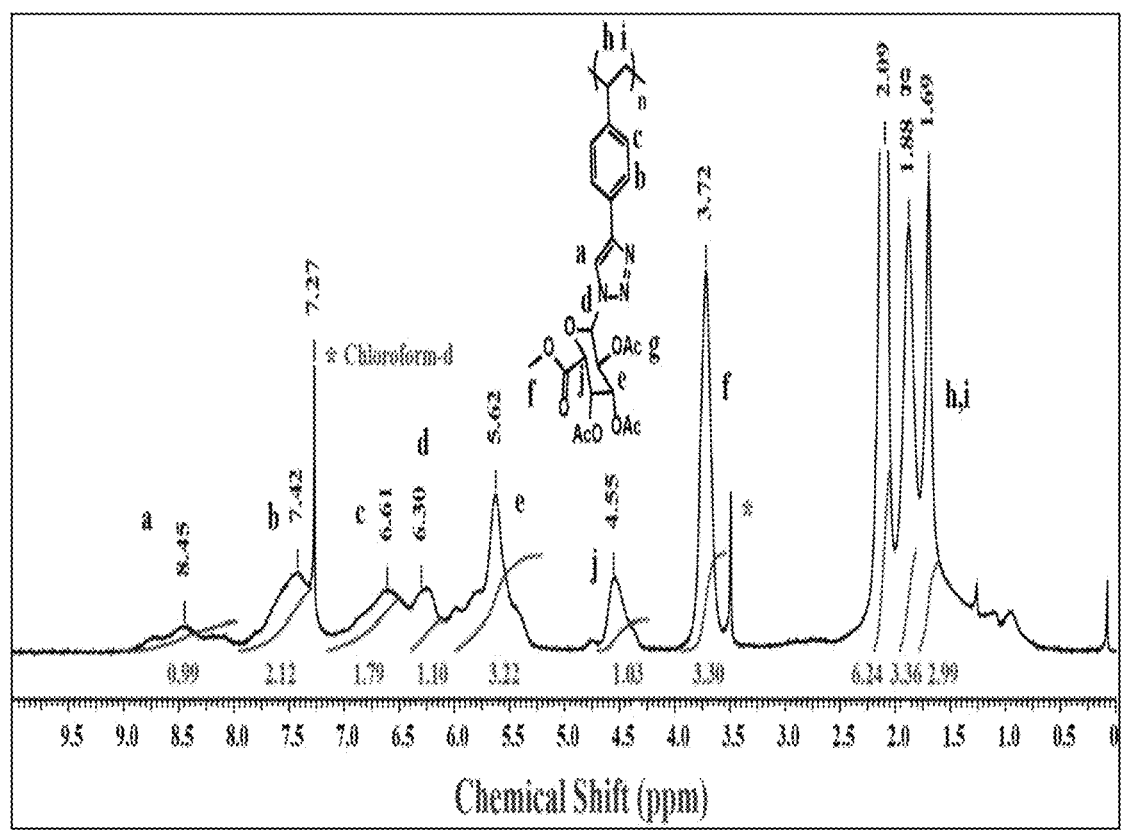
FIG. 1: $^1$H-NMR spectra of water soluble protected polymer surfactant (PS-PGlu) in $CDCl_3$.

PS-PGlu: Protected polymer surfactant of formula (I) comprising hydrophobic polystyrene and hydrophilic glucuronic acid units joined together with a triazole moiety;
PS-DGlu: Polymer surfactant of formula (I) comprising hydrophobic polystyrene and hydrophilic glucuronic acid units joined together with a triazole moiety;
PS: Polystyrene;
OPV: oligo (p-phenylenevinylene);
FRET: fluorescence resonance energy transfer;
PSG-OPV-n: glucuronic acid functionalized polystyrenenanobead covalently incorporating (oligo) p-phenylenevinylene (OPV);
FESEM: Field emission scanning electron microscopy;
RT: room temperature i.e., 25-30° C.

DETAILED DESCRIPTION OF THE INVENTION WITH THE ACCOMPANYING DRAWINGS

The invention will now be described in detail in connection with certain preferred and optional embodiments, so that various aspects thereof may be more fully understood and appreciated.

The term pendent refers to hanging or suspended or the point of attachment, with the point or end hanging downwards.

The term mini-emulsion refers to a process of polymerization, in which monomer droplets are dispersed in a continuous aqueous phase and are kept colloidally stable through the use of a surfactant and are stabilized using a co-stabiliser like hexadecane.

The term polymerization refers to a process of reacting monomer molecules together in a chemical reaction to form polymer chains or three-dimensional networks.

The term quenching refers to any process which decreases the fluorescence intensity of a given substance.

The term nanosensor refers to nanoscale devices that can measure any physical quantities and convert those quantities to signals that can be detected and analyzed.

The term bead refers to droplets of monomer dispersed in aqueous medium which is stabilized by surfactant and co-stabilizer. Polymerization happens inside the monomer beads in a mini-emulsion polymerization technique. So eventually, the mini-emulsion polymerization results in a polymer beads.

The term reflux refers to thermally accelerate the reaction by conducting it at an elevated, controlled temperature (i.e. the solvent's boiling point) and ambient pressure without losing quantities of the mixture.

Accordingly, the present invention provides a water soluble polymer surfactant (PS-DGlu) of formula (I) comprising hydrophobic polystyrene and hydrophilic D-glucuronic acid units joined together with a triazole moiety,

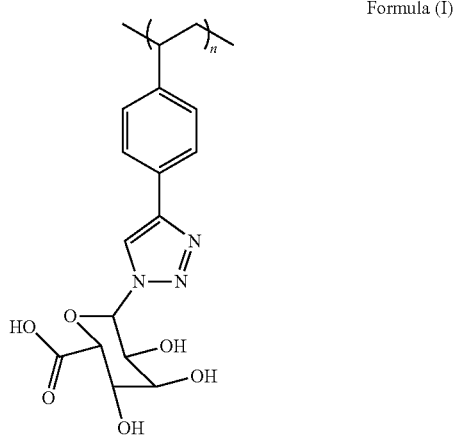

Formula (I)

wherein n is 30-50.

In the polymer surfactant (PS-DGlu), ratio of hydrophobic polystyrene and hydrophilic D-glucuronic acid units is preferably 1:1, wherein the hydrophilic D-glucuronic acid units act as a pendent moiety.

The present invention further provides a process for preparation of the polymer surfactant (PS-DGlu) of formula (I) and application thereof.

The water soluble polymer surfactant of formula (I) with glucoronic acid pendent is synthesized by solvent based free radical polymerization process.

In an embodiment, the present invention provides a process for preparation of the water soluble polymer surfactant (PS-DGlu) of formula (I) comprising the steps of:

a) adding iodine solution to the mixture of D-glucuronic acid and acetic anhydride at a temperature in the range of 0° C. to −5° C.; stirring the resultant mixture at a temperature in the range of 0° C. to −5° C. for a time period ranging from 2 to 3 hours and continuing the stirring at a temperature in the range of 25° C. to 30° C. for a time period ranging from 3 to 4 hours to afford penta-acetate glucuronic acid (1);

b) refluxing the solution of penta-acetate glucuronic acid (1) obtained in step (a) in dry methanol at a temperature in the range of 80° C. to 90° C. for a time period ranging from 24 to 26 hours to afford 1, 2, 3, 4-Tetra-O-acetyl-methyl-β-D-glucuronide (2);

c) adding TMS-azide and tin (IV) chloride to a solution of 1, 2, 3, 4-Tetra-O-Acetyl-methyl-β-D-Glucuronide (2) obtained in step (b) in a solvent followed by stirring the resultant mixture at a temperature in the range of 25 to 30° C. for a time period ranging from 15 to 20 hours to afford 2, 3, 4-tri-O-acetyl-1-azido-1-deoxy-β-D-glucuronic acid methyl ester (3);

d) heating a reaction mixture of 4-bromostyrene, ethynyltrimethylsilane, copper(I) iodide and triethyl amine at a temperature in the range of 50 to 60° C. for a time period ranging from 5 to 15 minutes followed by adding bis(triphenylphosphine) palladium (II) dichloride; stirring the reaction mixture at a temperature in the range of 50 to 60° C. for a time period ranging from 16 to 17 hours to afford 4-(trimethylsilane)ethynylstyrene (4);

e) adding tetra-n-butyl ammonium fluoride to a solution of 4-(Trimethylsilane)ethynylstyrene (4) obtained in step (d) in a solvent followed by stirring the reaction mixture at a temperature in the range of 25 to 30° C. for a time period ranging from 1 to 2 hours to afford 4-ethynylstyrene (5);

f) adding mixture of copper sulfate and sodium ascorbate in water to the solution of 4-ethynylstyrene (5) obtained in step (e) and 2, 3, 4-tri-O-acetyl-1-azido-1-deoxy-β-D-glucuronic acid methyl ester (3) obtained in step (c) in a solvent; stirring the resultant reaction mixture at a temperature in the range of 25° C. to 30° C. for a time period ranging from 24 to 25 hours to afford (2R, 3S, 4R, 5S, 6R)-2-(methoxycarbonyl)-6-(4-(4-vinylphenyl)-1H-1,2,3-triazol-1-yl)tetrahydro-2H-pyran-3,4,5-triyl tri acetate (6);

g) heating the reaction mixture of (2R, 3S, 4R, 5S, 6R)-2-(methoxycarbonyl)-6-(4-(4-vinylphenyl)-1H-1, 2,3-triazol-1-yl)tetrahydro-2H-pyran-3,4,5-triyl triacetate (6) obtained in step (f), AIBN and a solvent at a temperature in the range of 80° C. to 90° C. for a time period ranging from 24 to 25 hours to afford protected polymer (7) and;

h) adding solution of sodium methoxide in a solvent into a solution of protected polymer (7) obtained in step (g) in a solvent; stirring the resultant reaction mixture at a temperature in the range of 25° C. to 30° C. for a time period ranging from 8 to 10 hours to afford the polymer; dissolving the obtained polymer in a solvent followed by adding hydrochloric acid; stirring the reaction mixture at a temperature in the range of 25 to 30° C. for a time period ranging from 24 to 25 hours to afford water soluble polymer surfactant (PS-DGlu) of formula (I).

In a preferred embodiment, the solvents used in steps b-h are selected from methanol, dichloromethane, tetrahydrofuran, dimethyl formamide, water or combination therefrom.

In another preferred embodiment, the acid used in step (h) is hydrochloric acid.

Step wise reaction scheme of preparation of water soluble polymer surfactant of formula (I) is Shown in FIGS. 21 & 22.

In an embodiment, the PS-DGlu polymer shows high molecular weight and also shows good photo stability in water dispersion.

In another embodiment, the PS-DGlu polymer dispersion shows exceptionally good stability in physiological medium.

In one embodiment the present invention provides hydrophilic-Lipophylic balance value calculation by Griffin's Method. According to Griffin's scale if HLB value falls in the range of 8-16 it can act as surfactant for oil in water emulsion polymerization. As PS-DGlu in present invention shows HLB value 14.05 it clearly shows that it can also acts as surfactant.

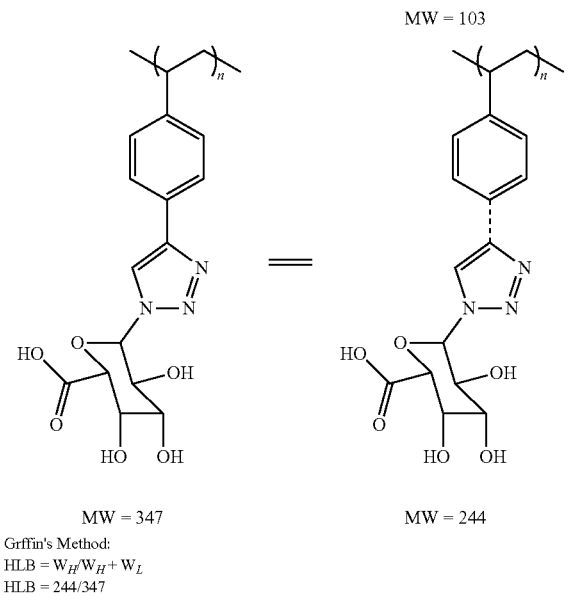

Grffin's Method:
HLB = $W_H/W_H + W_L$
HLB = 244/347
HLB = 14.05

In an embodiment, the glucuronic acid functionalized polystyrene (PS-DGlu) surfactant is used for synthesizing glucuronic acid functionalized polystyrene nanobeads covalently incorporating (oligo) p-phenylenevinylene sensor (PSG-OPV-n) by mini-emulsion polymerization comprising the steps of:

a) preparing organic phase comprising styrene, a co-stabilizer and polymerizable (oligo) p-phenylenevinylene (OPV) dye;

b) preparing aqueous phase comprising an initiator and glucuronic acid functionalized polystyrene (PS-DGlu) polymer in water;

c) adding organic phase as obtained in step (a) drop-wise to the aqueous phase as obtained in step (b) and pre-emulsifying at a temperature in the range of 21° C. to 25° C. followed by sonication under ice cooled condition to obtain a mini-emulsion;

d) polymerization of the mini-emulsion obtained in step (c) at 70° C. for 20 h with a stirring speed of 750 rpm; and e) quenching the polymerization reaction of step (d) and purifying the obtained latex to obtain nanosensor (PSG-OPV-n) beads.

In a preferred embodiment, quenching is achieved by adding two drops of 1 wt % hydroquinone to the reaction mixture. Further, the latex product obtained is purified by dialysis using 6 kD MW cut-off membrane for three days to obtain PSG-OPV-n.

In an embodiment, the said co-stabilizer used is selected from the group consisting of hexadecane, cetyl alcohol, dodecyl methacrylate or stearyl methacrylate.

In an embodiment, during the process to obtain PSG-OPV-n nanobeads the initiator used in selected from the group consisting of 4,4'-Azobis(4-cyanovaleric acid) (ACVA), azobisisobutyronitrile (AIBN), potassium peroxydisulfate (KPS), lactoperoxidase (LPO) or benzoyl peroxide (BPO).

In an embodiment, the present w/w ratio of glucuronic acid functionalized polystyrene (PS-DGlu) to (oligo) p-phenylenevinylene (OPV) is 1-5:3 in the PSG-OPV-n nanobeads.

In an embodiment, the size of the PSG-OPV-n nanobeads is in the range of 163 to 328 nm.

Figure 23:
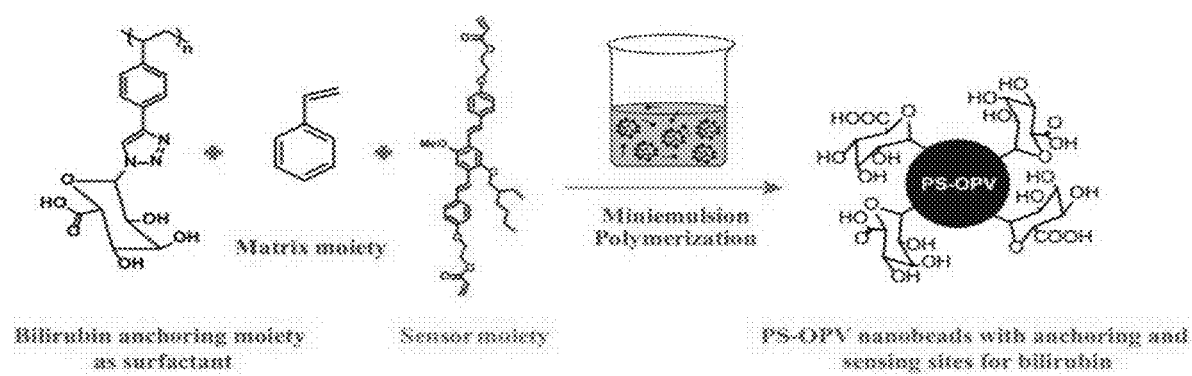
FIG. 23: Synthesis of glucuronic acid functionalized PS nanobeads incorporating OPV (PSG-OPV-n) via mini-emulsion polymerization.

Synthesis of glucuronic acid functionalized PS nanobeads incorporating OPV (PSG-OPV-n) via mini-emulsion polymerization is illustrated in FIG. 23.

Different amounts of PS-DGlu with fixed amount of styrene and OPV were used to prepare a series of functionalized PS nanobeads (PSG-OPV-1 to PSG-OPV-5) using 4-4' azobis(4-cyanovaleric acid) (ACVA) and hexadecane (HD) as initiator and co-stabilizer respectively (Table 1).

TABLE 1 showing the sample designation, Dye Loading Content (DLC), Size and its polydispersity index (PDI), solid content, zeta potential ($\zeta$).

| Samples | PS-DGlu (mg) | OPV Dye in feed (mg) | Dye incorporated (mg) | DLC (%) | Size (nm) | PDI | Solid Content (%) | $\zeta$-potential (mV) |
|---|---|---|---|---|---|---|---|---|
| PSG-OPV-1 | 10 | 30 | 11.4 | 0.11 | 163.4 | 0.06 | 6 | −35.4 |
| PSG-OPV-2 | 20 | 30 | 7.8 | 0.08 | 221.6 | 0.05 | 10 | −52.1 |
| PSG-OPV-3 | 30 | 30 | 8.2 | 0.08 | 224.1 | 0.05 | 6 | −36.0 |
| PSG-OPV-4 | 40 | 30 | 6.7 | 0.07 | 328.0 | 0.07 | 8 | −47.5 |
| PSG-OPV-5 | 50 | 30 | 8.8 | 0.09 | 192.0 | 0.06 | 20 | −55.0 |

Figure 6:
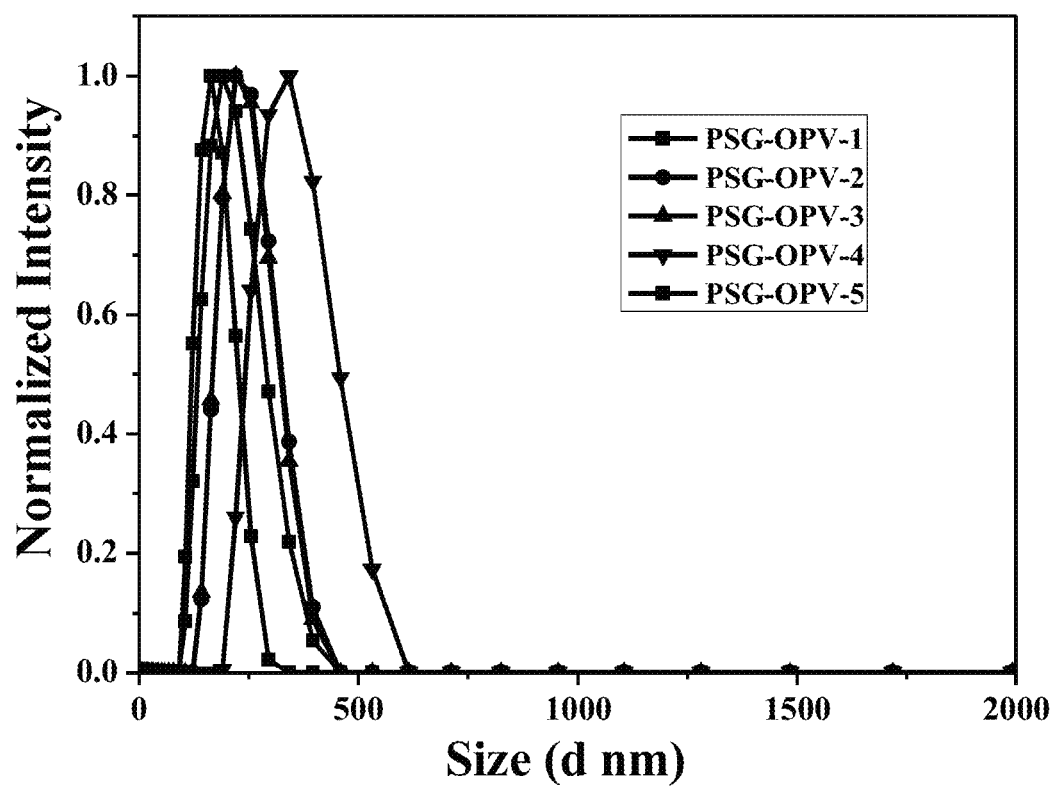
FIG. 6: FESEM of PSG-OPV-n confirming micelle formation.
Figure 11:
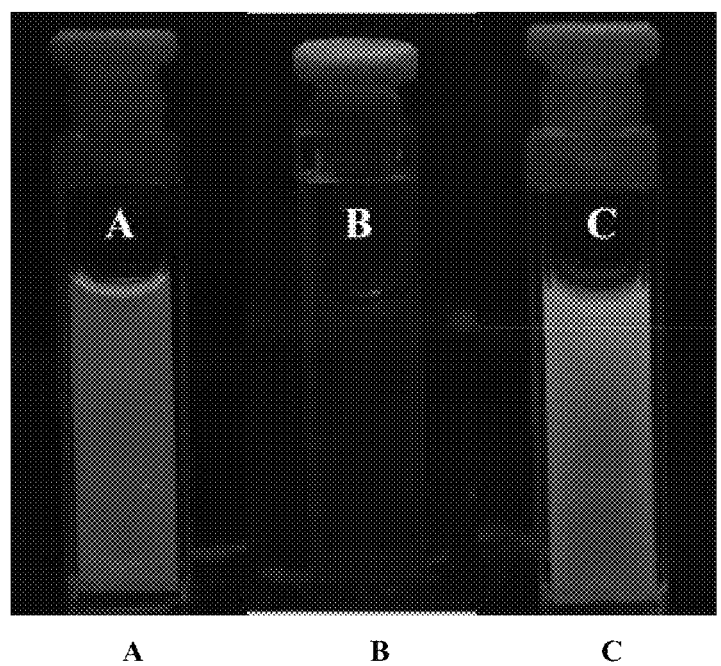
FIG. 11: Photograph showing (A) PSG-OPV-5 (Blue emission), (B) Bilirubin (no emission), and (c) PSG-OPV-5 after bilirubin addition (bluish green emission) in ches buffer at pH 10.
Figure 12:
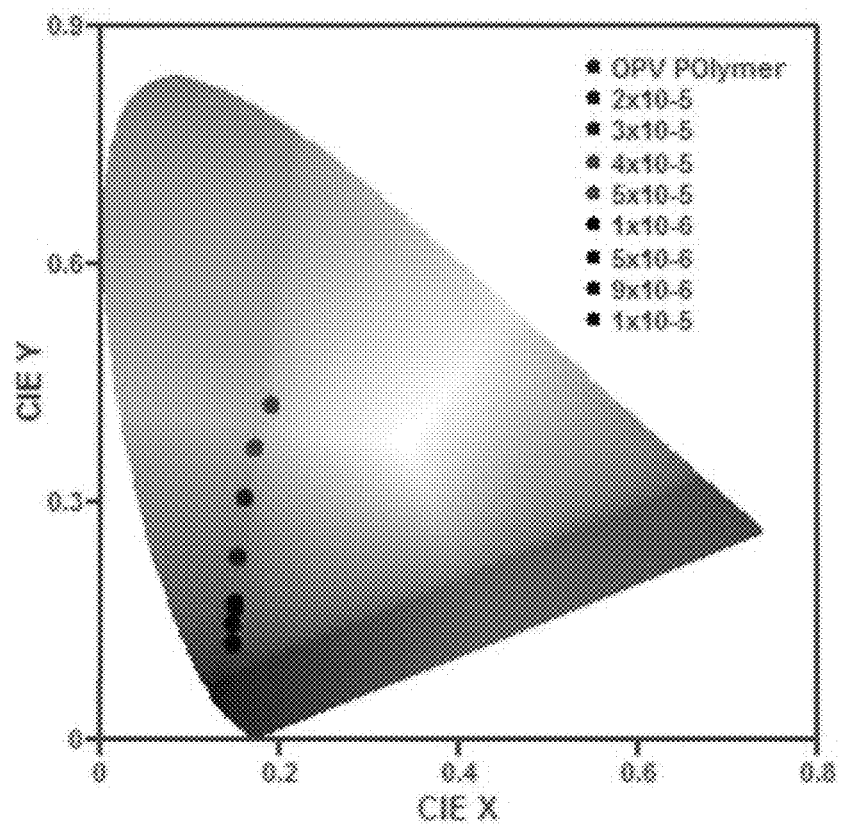
FIG. 12: CIE co-ordinate diagram of PSG-OPV-5 with or without varying bilirubin concentrations.

The DLC refers to dye loading content, and based on the above values, very less amount of the OPV dye can result in the required function—fluorescence color change based detection. The size and stability of the obtained PS nanobeads is analyzed by DLS measurement in water (FIG. 6). Size of all the nanobeads (PSG-OPV-1 to PSG-OPV-5) are within nanometer range, varying from 160 to 328 nm and PDI values remained below 0.1 showing monodisperse particles. Polystyrene polymer (PS-DGlu) stabilized the PS nanobeads in the size range of 160-328 nm and surface functionalized the nanobeads with glucuronic acid together with successful covalent incorporation of OPV as fluorophore in styrene mini-emulsion polymerization. Among series of PSG-OPV-n, PSG-OPV-5 is having higher zeta potential, solid content, molecular weight and OPV incorporation in comparison to other nanobeads. Instant visual detection of bilirubin under UV lamp by blue emission of polymer turned bluish green instantly after bilirubin addition (FIGS. 11 and 12).

The present invention further provides a process for the detection of bilirubin using glucuronic acid functionalized polystyrene nanobead covalently incorporating (oligo) p-phenylenevinylene (OPV) i.e. PSG-OPV-n. The bilirubin detection is carried out by synthesis of water soluble polystyrene polymer (PS-DGlu) beads in presence of OPV to produce nanosensor beads. Detection of bilirubin is carried out by using PSG-OPV-n via facilitating energy transfer (FRET) from OPV [oligo (p-phenylenevinylene)] to bilirubin. OPV is used as sensing material due to its spectral overlap with bilirubin thus favoring energy transfer process. The OPV fluorophore works as signal transducer while glucuronic acid works on the surface of PS nanobeads as an interaction site for free bilirubin to facilitate non-covalent interaction via hydrogen bonding. Detection of bilirubin is carried out by using polystyrene nanobeads via facilitating energy transfer from OPV [oligo (p-phenylenevinylene)] (sensor) to bilirubin (acceptor). OPV not only serves as a fluorescent cross-linker but also facilitates energy transfer pair to bilirubin. The change in emission and absorption intensity of polymer after the addition of different concentrations of bilirubin were recorded at 18° C. with slit width of 1 nm. Emission spectra showed marked decrease in OPV emission with the increasing concentration of bilirubin.

In another embodiment, the present invention provides a glucuronic acid functionalized polystyrene nanobead covalently incorporating (oligo) p-phenylenevinylene (OPV) nanosensor (PSG-OPV-n) beads, comprising: a glucuronic acid functionalized polystyrene (PS-DGlu) polymer and polymerizable (oligo) p-phenylenevinylene (OPV) dye, which enabled the detection of bilirubin with the detection limit in the range of 150 nM to 20 nM, and preferably, the detection limit is 20 nM.

In another embodiment, the glucuronic acid functionalized PS based nanosensor bead exhibited one of the highest quenching constant values with value as high as Ksv=262008.

In one embodiment, the present invention provides a process for the detection of bilirubin using PS-OPV-n comprising the steps of:
 a. preparing sample solution in water or buffer at pH=10 by the addition of NaOH;
 b. titrating polystyrene functionalized with glucuronic acid polymeric solution in distilled water or buffer with the sample solution and
 c. determining by fluorimetry, quenching of fluorescence intensity at 446 nm.

The bilirubin stock solution concentration ranges from $1\times10^{-6}$ M to $3\times10^{-5}$ M. An instant quenching of ≈36% was observed at concentration of $3\times10^{-6}$ M which finally reached to >50% quenching at $5\times10^{-6}$ M and the almost 97% quenching at 3×10-5 M (FIG. 10D). In the PS based bilirubin sensor, only surface bound fluorophore (OPV) was involved in energy transfer to bilirubin, so that some unquenched OPV would add up in enhanced green emission of bilirubin resulting in blue green emission to attain efficient visual detection of bilirubin in human blood serum.

The efficient FRET (fluorescence resonance energy transfer) is carried out from PSG-OPV-n polymer to bilirubin leading to spectral overlap between emission of OPV and absorption of bilirubin resulting in the quenching of emission of the polystyrene with simultaneous weak emission from bilirubin. The color is changed from blue to bluish green under UV lamp after addition of bilirubin into polymer. Sensor selectivity is observed using glucose, sucrose, metal ions, cholesterol and biliverdin. The limit of detection is low as 20 nM which is less than clinical range for causing jaundice. The developed sensor shows its effectiveness towards real time monitoring of free bilirubin in human serum.

In an embodiment, a kit for the detection of bilirubin using glucuronic acid functionalized polystyrene nanobead covalently incorporating (oligo) p-phenylenevinylene (OPV) iePSG-OPV is provided which comprises:
 a) stock solution of sensor (A) comprising glucuronic acid functionalized polystyrenenanobead covalently incorporating (oligo) p-phenylenevinylene (OPV);
 b) graduated dropper (B);
 c) analyte chamber (C) and
 d) UV chamber at the bottom (D)

In yet another embodiment, the present invention provides the detection of bilirubin using glucuronic acid functionalized polystyrenenanobead covalently incorporating (oligo) p-phenylenevinylene (OPV) i.e. PSG-OPV by using kit comprising the steps of:
 a. adding sample into stock solution of sensor comprising glucuronic acid functionalized polystyrenenanobead covalently incorporating (oligo) p-phenylenevinylene (OPV) sensor with the help of a dropper;
 b. pouring the solution of step (a) to analysis chamber equipped with an UV chamber at the bottom and
 c. detecting change in blue emission of the polymer.

FIG. 1 depicts $^1$H NMR spectrum of polystyrene with protected D glucuronic acid (PS-PGlu) in $CDCl_3$.

Figure 2:
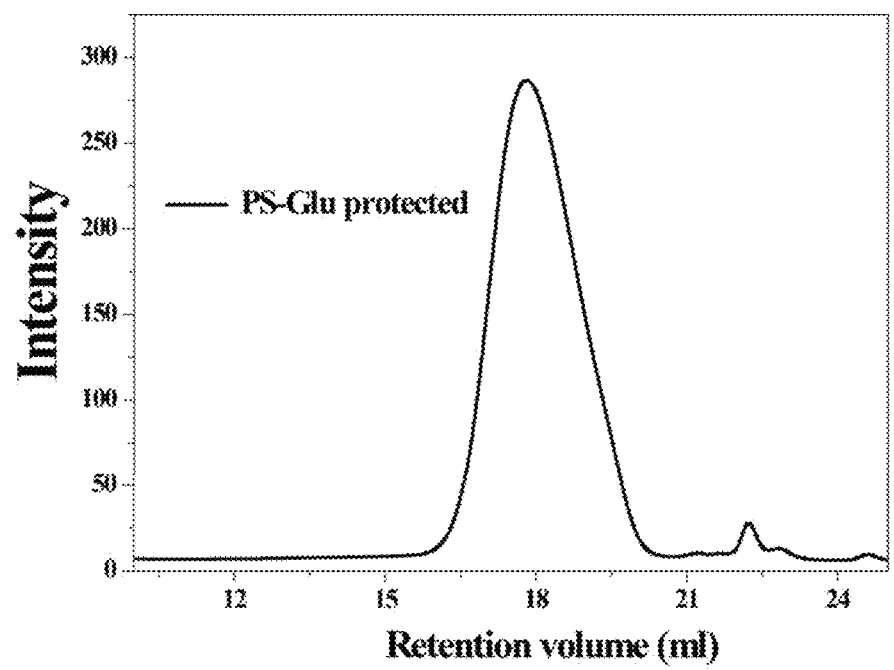
FIG. 2: Gel permeation chromatography (GPC) of water soluble protected polymer surfactant PS-PGlu.

FIG. 2 depicts gel permeation chromatography (GPC) of PS-PGlu. The molecular weight, determined by GPC showed an $M_n$ value of 16,800 with a polydispersity index (PDI) value of around 1.8.

Figure 3:
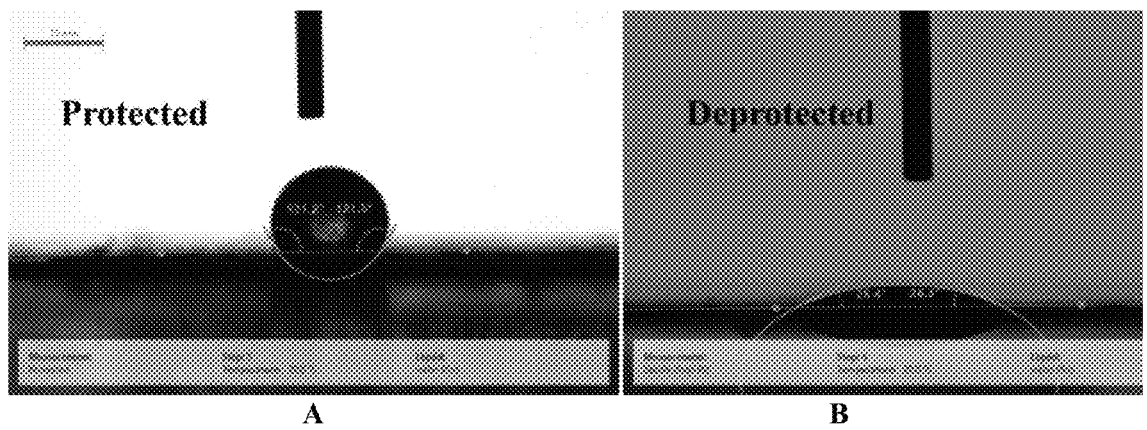
FIG. 3: Contact angle studies showing comparison between (A) protected polymer (PS-PGlu) and (B) deprotected polymer (PS-DGlu).

FIG. 3 depicts contact angle studies showing comparison between deprotected and protected polymer where protected polymer showed higher angle signifying its hydrophobicity and for deprotected polymer contact angle almost flattened signifying appreciable hydrophilicity. Contact angle drastically changed from 121° for PS-PGlu to 26.4° for the PS-DGlu polymer because of the transition from a hydrophobic to hydrophilic environment.

Figure 4:
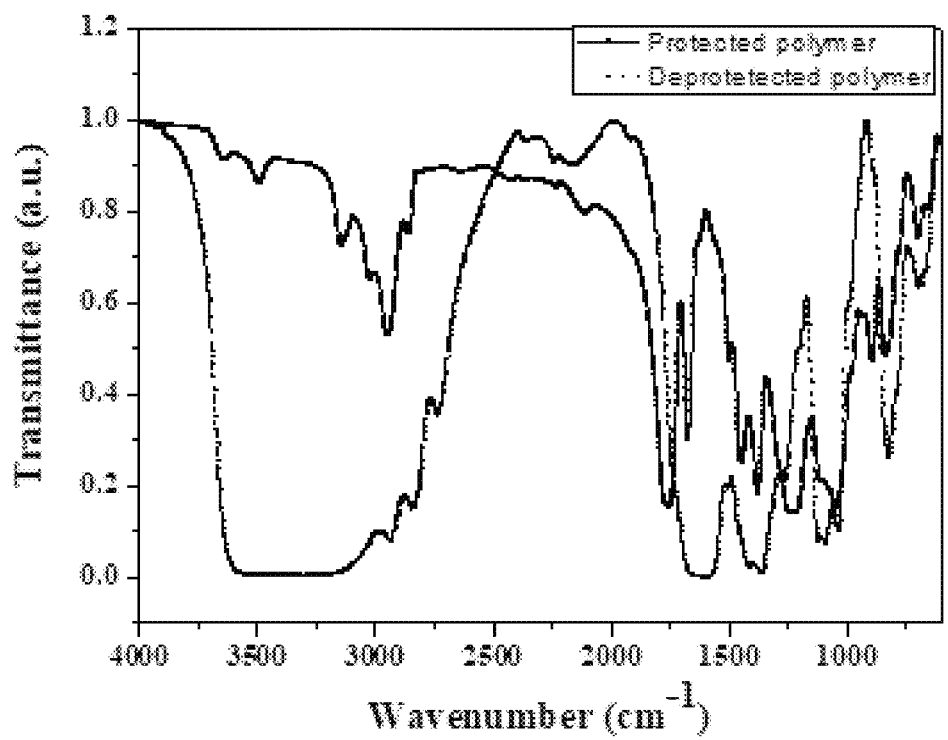
FIG. 4: FTIR spectrum showing comparison between deprotected polymer (PS-DGlu) and protected polymer (PS-PGlu).

FIG. 4 depicts FTIR spectrum showing comparison between deprotected (PS-DGlu) and protected polymer (PS-PGlu) where broad peak around 3000 $cm^{-1}$ signify the presence of OH group and peak around 1680 $cm^{-1}$ signify presence of carbonyl of COOH group.

Figure 5:
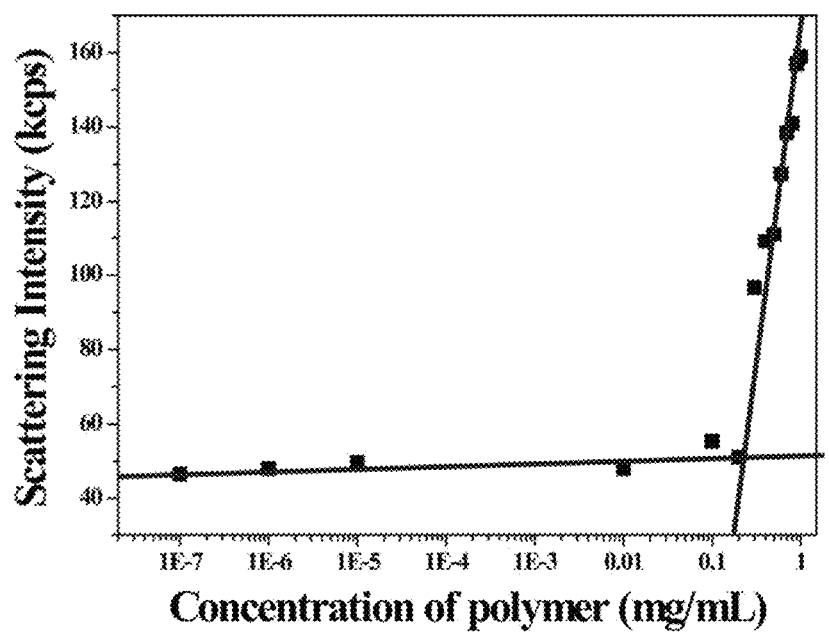
FIG. 5: Critical micellar concentration value determination for PS-DGlu by dynamic light scattering (DLS).

FIG. 5 depicts critical micellar concentration (CMC) value determination of PS-DGlu by dynamic light scattering (DLS). By DLS the CMC was found to be 0.2 mg/mL. With the formation of micelle in the solution, a sudden change in the scattering intensity is highly expected, thus the minimum concentration of polymer, at which the scattered intensity sharply increased, was used to evaluate CMC. The point of the intersection of two linear regression lines was considered as the CMC of the polymer, and it was found to be 0.2 mg/mL. This low value of the CMC further justified ability of PS-DGlu to act as a surfactant and thereby stabilize the mini-emulsion.

FIG. 6 depicts dynamic light scattering (DLS) of PSG-OPV polymers in ches buffer at pH 10.

Figure 7:
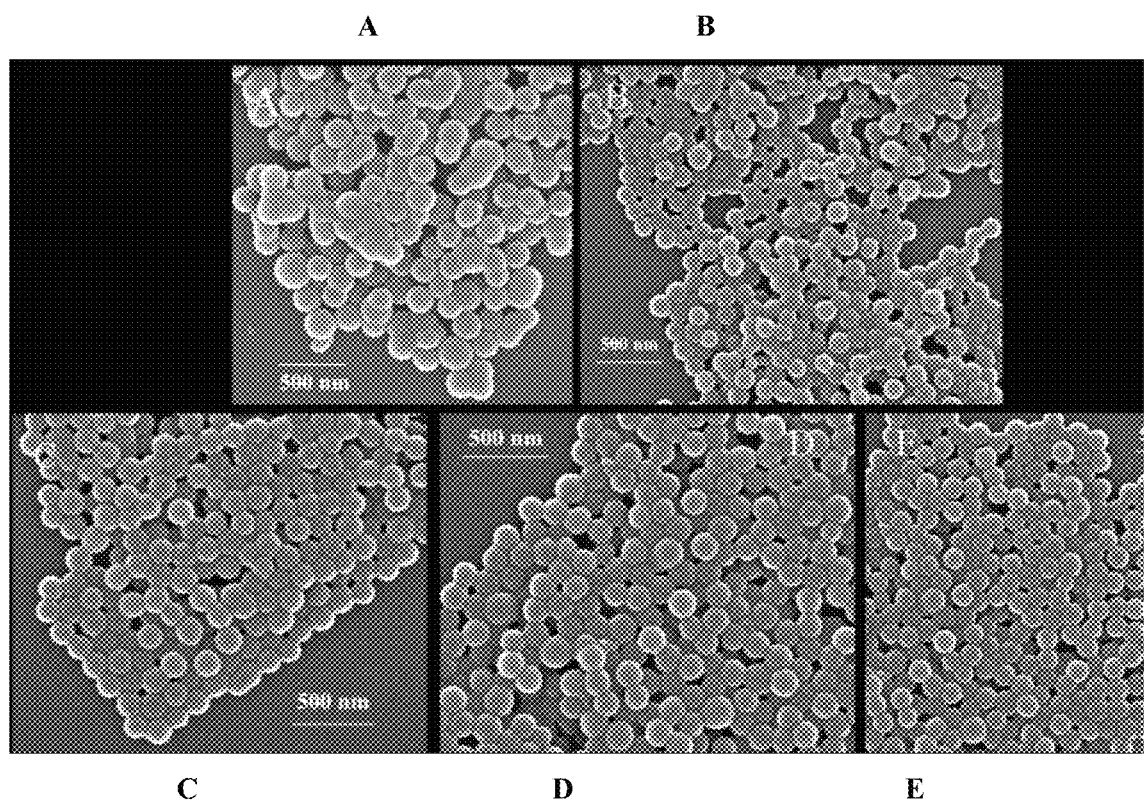
FIG. 7: Dynamic light scattering (DLS) of PSG-OPV-n polymers in ches buffer at pH 10 (A-E).

FIG. 7 depicts FESEM of Polystyrene with D-glucuronic acid homopolymer loading hydrophobe (OPV) confirming their micelle formation. Micellar nature was confirmed by FESEM as it was capable of loading the hydrophobic dye (OPV) and formed spherical morphology when drop casted on silicon wafer.

Figure 8:
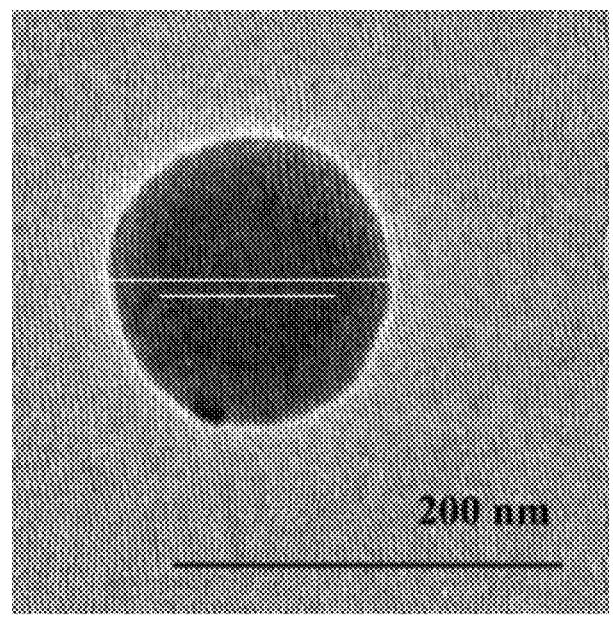
FIG. 8: TEM image showing core shell structure of representative PSG-OPV-5 sample.

FIG. 8 depicts TEM image showing core shell structure of representative PSG-OPV-5 sample. A clear core-shell structure was discernible with a PS core diameter of 85 nm and an overall size of 133 nm, including a hydrophilic shell.

Figure 9:
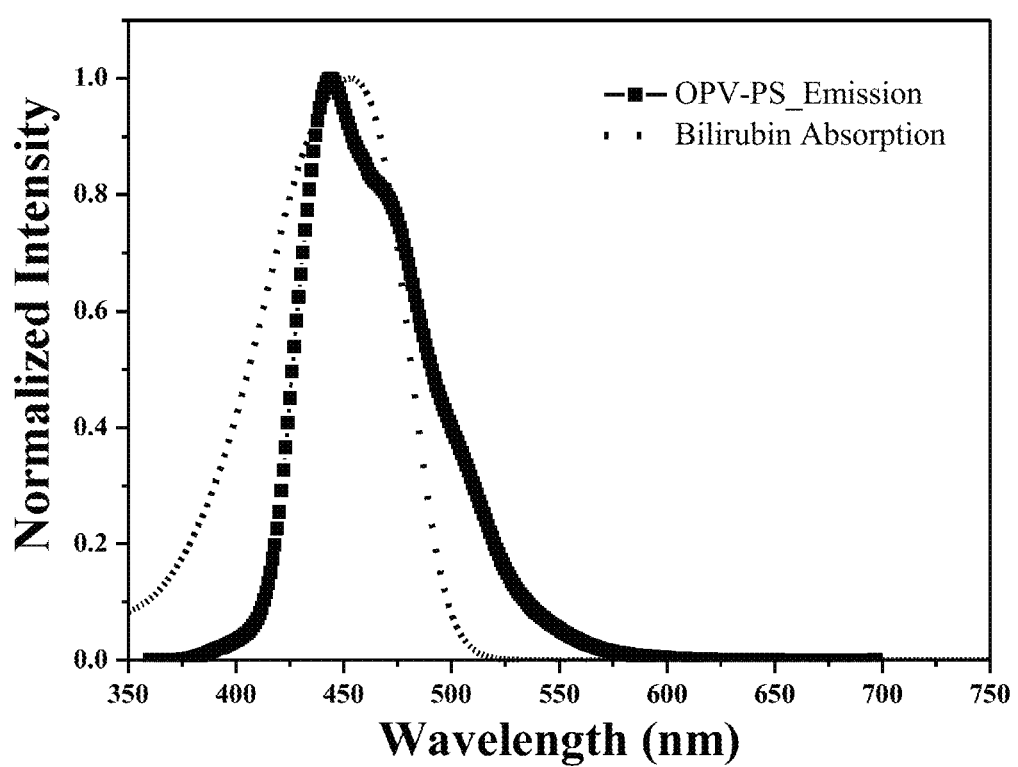
FIG. 9: Spectral overlap between emission spectra of PSG-OPV-5 and absorption spectra of bilirubin.

FIG. 9 depicts spectral overlap between emission spectra of PSG-OPV-5 and absorption spectra of bilirubin.

Figure 10:
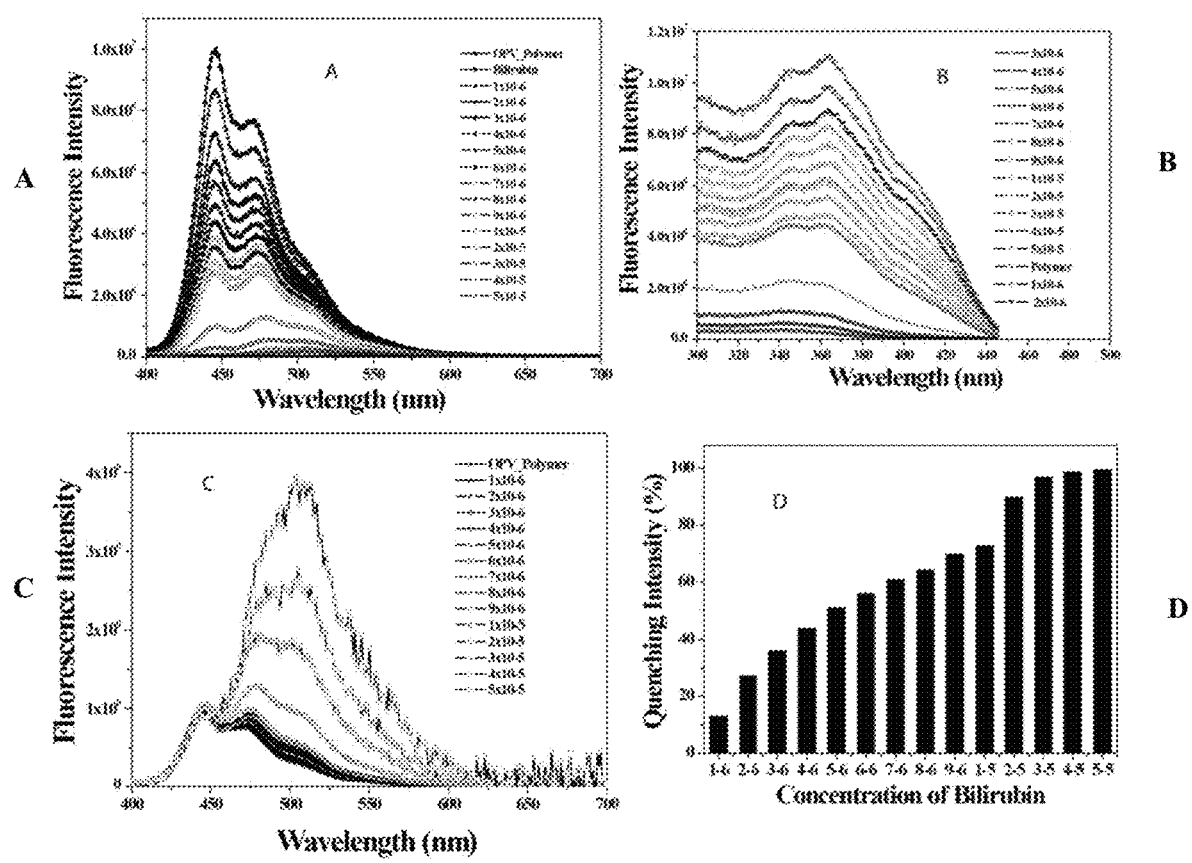
FIG. 10: (A) Emission and (B) excitation spectra of PSG-OPV-5 recorded after the addition of varying amount of bilirubin ($1\times10^{-6}$ M to $5\times10^{-5}$ M). (C) normalized emission spectra of PSG-OPV-5 recorded after the addition of varying amount of bilirubin ($1\times10^{-6}$ M to $5\times10^{-5}$ M) at 446 nm. (D) bar graph comparing the quenching intensity vs bilirubin concentration.

FIG. 10 depicts (a) Emission and (b) excitation spectra of PSG-OPV-5 recorded after the addition of varying amount of bilirubin ($1\times10^{-6}$ M to $5\times10^{-5}$ M). With the increase in bilirubin concentration, OPV emission and excitation intensity decreased. (c) normalized emission spectra of PSG-OPV-5 recorded after the addition of varying amount of bilirubin ($1\times10^{-6}$ M to $5\times10^{-5}$ M) at 446 nm. On normalizing emission spectra of OPV at 446 nm; one could clearly see the enhancement in bilirubin emission. (d) bar graph comparing the quenching intensity vs bilirubin concentration Thus one could observe enhancement of quenching intensity of OPV on increasing bilirubin concentration.

FIG. 11 depicts photograph showing (a) PSG-OPV-5 (Blue emission) (b) Bilirubin (no emission) (c) PSG-OPV-5 after bilirubin addition (bluish green emission) in ches buffer at pH 10.

FIG. 12 depicts CIE co-ordinate diagram of PSG-OPV-5 without and with varying bilirubin concentrations.

Figure 13:
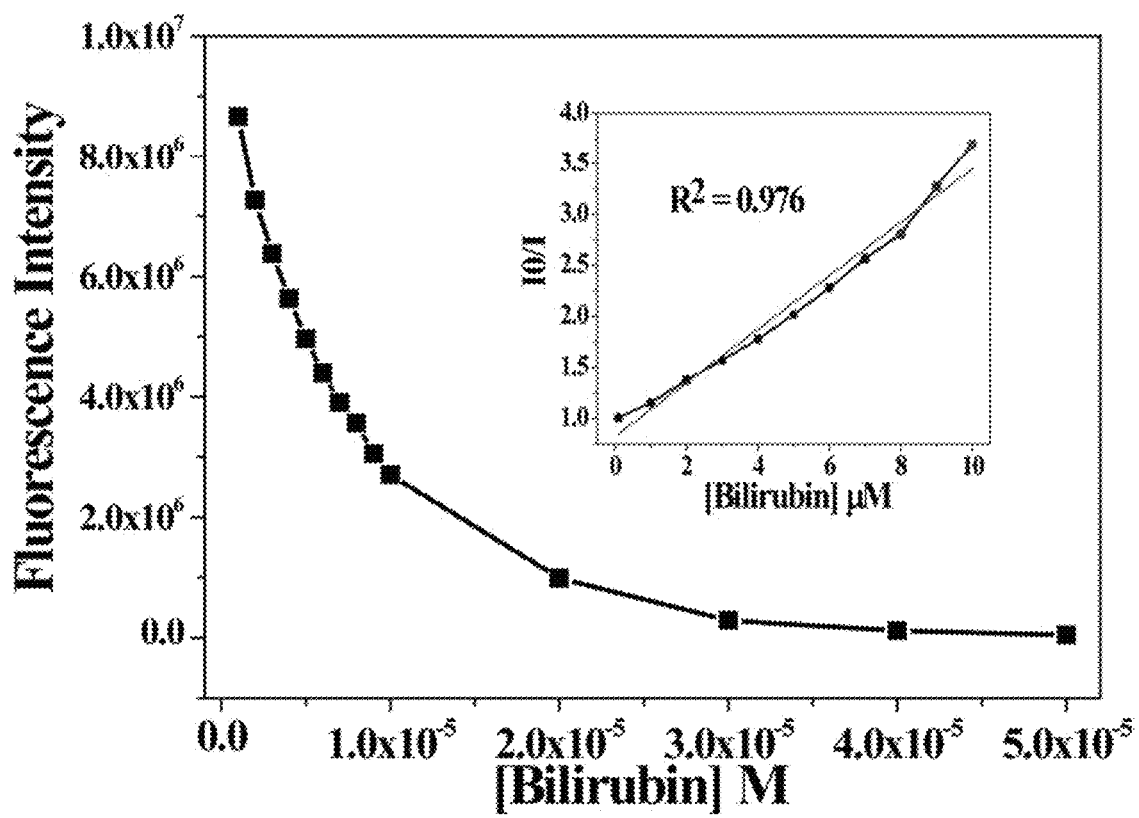
FIG. 13: Plot of changes in emission intensity of PSG-OPV-n vs. concentration of bilirubin and their linear range using SternVolmer equation.

FIG. 13 depicts Plot of changes in emission intensity of PSG-OPV vs. concentration of bilirubin and their linear range using Stern-Volmer equation.

Figure 14:
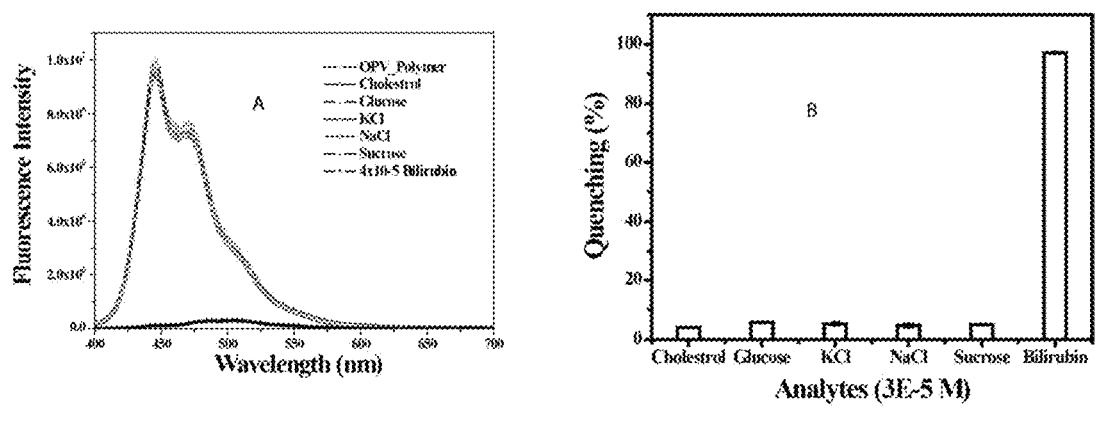
FIG. 14: (A) Emission spectra showing the selectivity against other interferences in ches buffer, and (B) bar graph showing the selectivity against other interferences in ches buffer. Each measurement is done twice and their average was plotted along with their standard deviation

FIG. 14 depicts emission spectra showing the selectivity against other interferences in ches buffer, (b) bar graph showing the selectivity against other interferences in ches buffer. Each measurement is done twice and their average is plotted along with their standard deviation. No appreciable quenching in OPV emission was observed in presence of other analytes.

Figure 15:
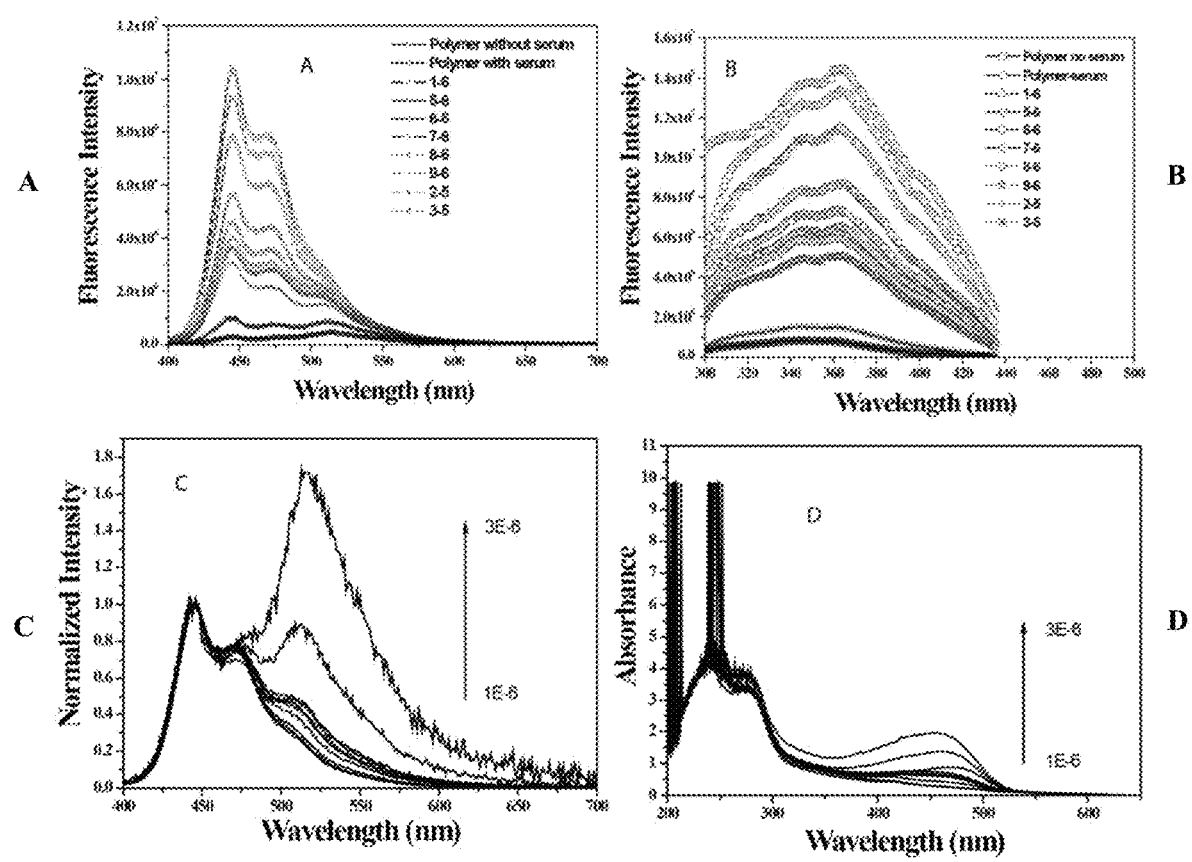
FIG. 15: (A) Emission, (B) excitation, (C) Normalized emission spectra, and (D) absorption spectra of PSG-OPV-5 recorded after the addition of varying concentrations of bilirubin ($1\times10^{-6}$ M to $3\times10^{-5}$ M) in human blood serum

FIG. 15 depicts emission, (b) excitation, (c) Normalized emission spectra, (d) absorption spectra of PSG-OPV-5 recorded after the addition of varying concentrations of bilirubin ($1\times10^{-6}$ M to $3\times10^{-5}$ M) in human blood serum. The claim in FIG. 1 has been reproduced in human blood serum.

Figure 16:
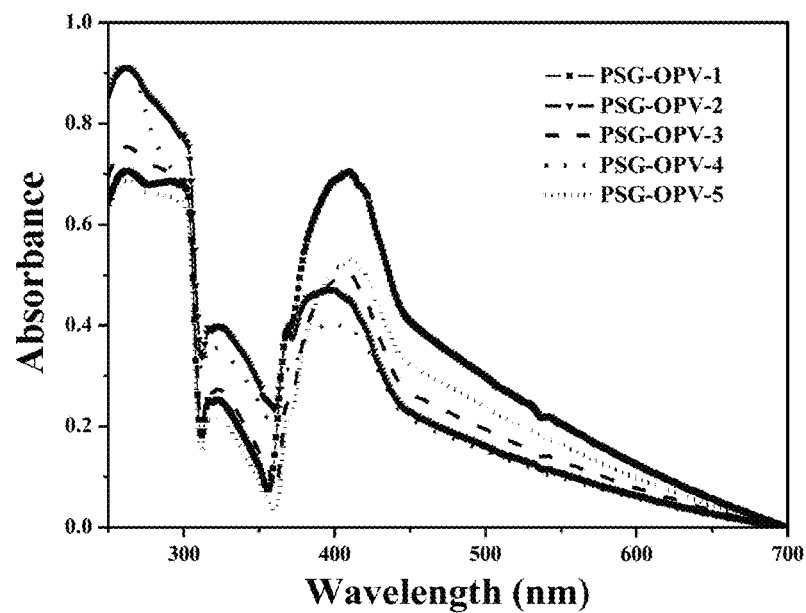
FIG. 16: Absorption spectra of PSG-OPV-n polymers in THF.

FIG. 16 depicts absorption spectra of PSG-OPV-n polymers in THF.

Figure 17:
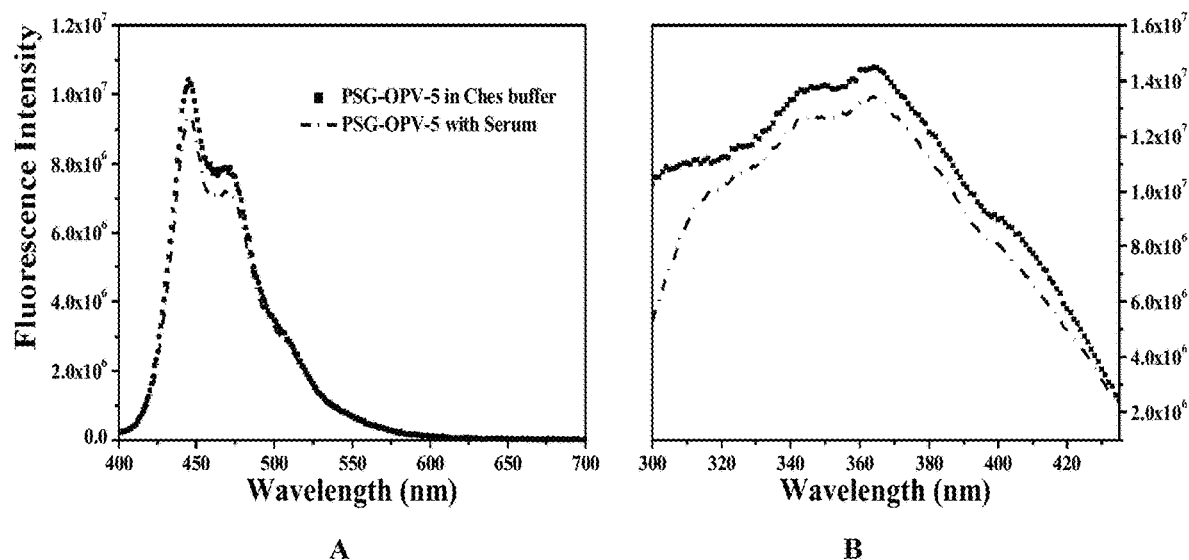
FIG. 17: Comparison of (A) emission and (B) excitation spectra of PSG-OPV-5 in ches buffer and human blood serum showing no significant difference in their intensity.

FIG. 17 depicts comparison of (a) emission and (b) excitation spectra of PSG-OPV-5 in ches buffer and human blood serum showing no significant difference in their intensity.

Figure 18:
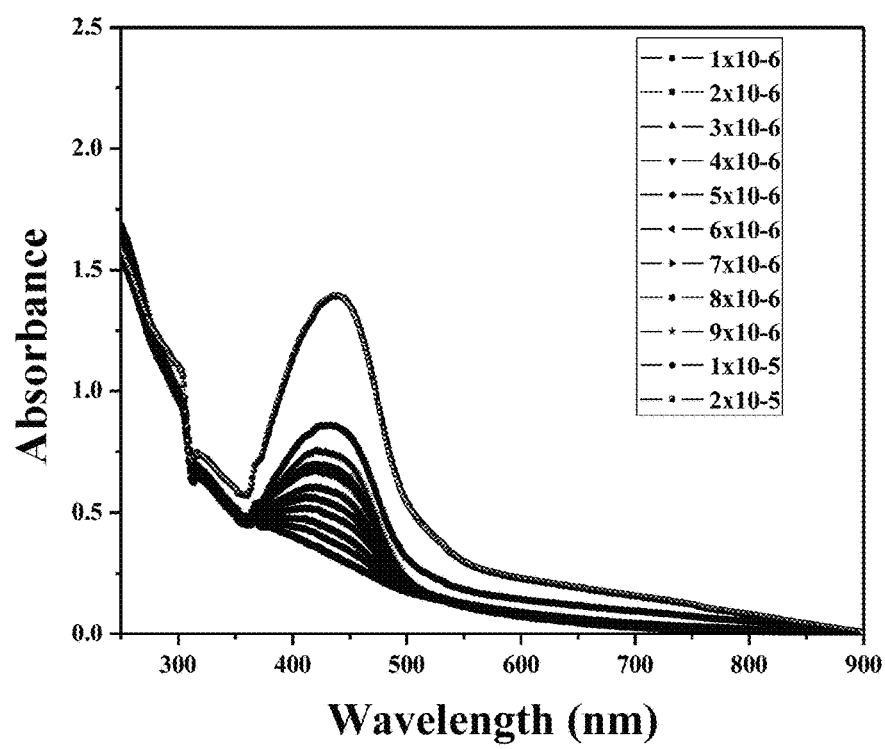
FIG. 18: Absorption spectrum of PSG-OPV-5 after addition of bilirubin in ches buffer.

FIG. 18 depicts absorption spectrum of PSG-OPV-5 after addition of bilirubin in ches buffer.

Figure 19:
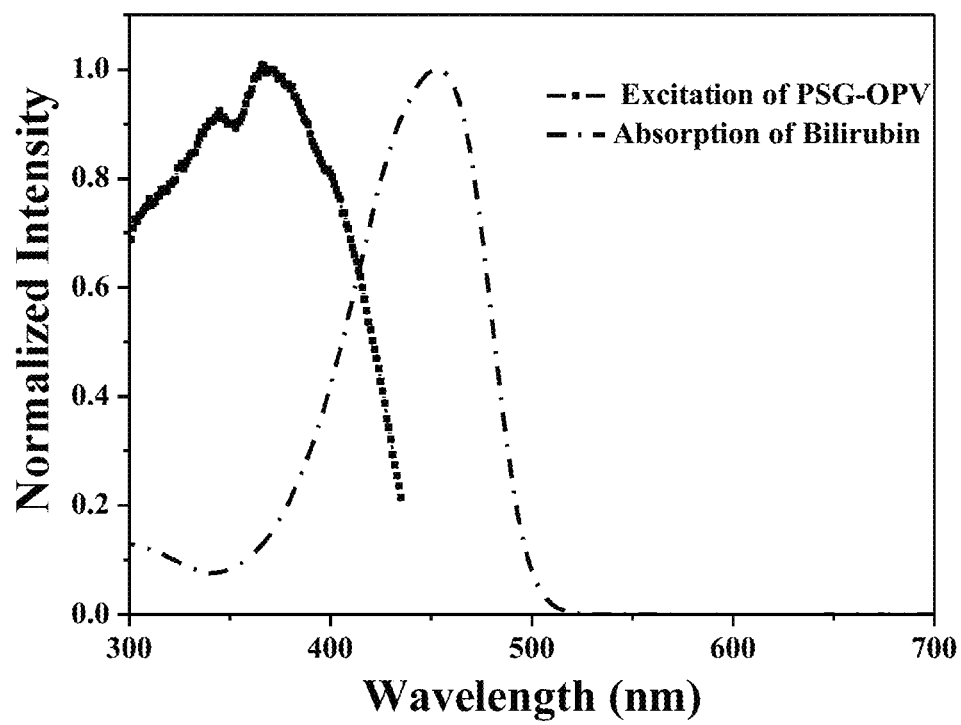
FIG. 19: Spectral overlap between excitation spectrum of PSG-OPV-5 and absorption spectrum of bilirubin in ches buffer.

FIG. 19 depicts emission spectra of PSG-OPV-5 recorded after the addition of same concentration of bilirubin vs biliverdin ($2\times10^{-5}$ M) in human blood serum.

Figure 20:
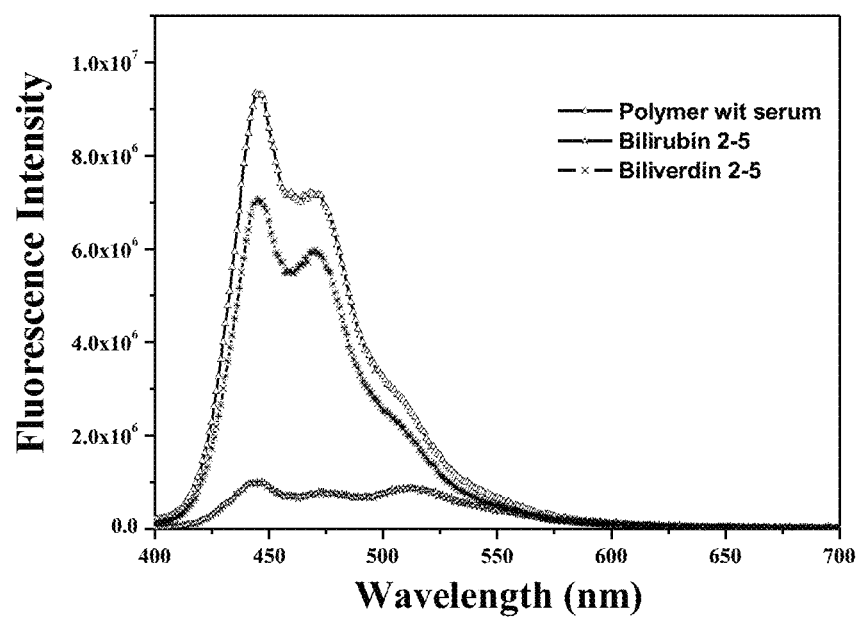
FIG. 20: Emission spectra of PSG-OPV-5 recorded after the addition of same concentration of bilirubin vs bliverdin ($2\times10^{-5}$ M) in human blood serum.

FIG. 20 depicts emission spectra of PSG-OPV-5 recorded after the addition of same concentration of bilirubin vs bliverdin ($2\times10^{-5}$ M) in human blood serum.

FIGS. 21 & 22: Schemes A-E: Step wise reaction synthesis for the preparation of water soluble polymer surfactant of formula (I).

FIG. 23: Synthesis of glucuronic acid functionalized PS nanobeads incorporating OPV (PSG-OPV-n) via mini-emulsion polymerization.

EXAMPLES

Following examples are given by way of illustration therefore should not be construed to limit the scope of the invention.

Example 1: Synthesis of penta-acetate Glucuronic Acid (1)

To 5 g of D-glucuronic acid was added 75 mL of acetic anhydride and the solution was stirred under ice cooled condition. Then iodine was slowly added and color of the solution became red. This was allowed to stir for 2 h at 0° C. and further 3 h at room temperature (28° C.). The excess of acetic anhydride was distilled off and rest of the mixture was dissolved in DCM. The organic layer was then washed three times with sodium thiosulfate pentahydrate to remove iodine and concentrated to dryness to give white solid. Yield: 80%. $^1$H NMR (200 MHz, CDCl$_3$): δ in ppm 5.80 (d, 1H), 5.36 (t, 1H), 5.28 (t, 1H), 5.11 (t, 1H), 4.32 (d, 1H), 2.26 (s, 3H), 2.12 (s, 3H), 2.03 (m, 9H). LC-MS/MS (in MeCN) m/z calculated–404.02; observed [M+Na]–427.08, [M+K]–443.06.

Example 2: Synthesis of 1, 2, 3, 4-Tetra-O-Acetyl-methyl-β-D-Glucuronide (2)

To the above penta-acetate product was added dry methanol and allowed to reflux for 24 h. The excess methanol was distilled off under vacuum. The product was purified by recrystallization from methanol. Yield: 60%. $^1$H NMR (200 MHz, CDCl$_3$): δ in ppm 5.26 (m, 2H), 4.97 (t, 1H), 4.71 (d, 1H), 4.14 (d, 1H), 3.78 (s, 3H), 2.08 (s, 3H), 2.04 (s, 6H). LC-MS/MS (in MeCN) m/z calculated–376.13; observed [M+Na]-399.08, [M+K]-415.06.

Example 3: Synthesis of 2, 3, 4-tri-O-acetyl-1-azido-1-deoxy-β-D-glucuronic Acid Methyl Ester (3)

To 2 g of 1, 2, 3, 4-Tetra-O-Acetyl-methyl-β-D-Glucuronide was added 35 mL of dry DCM under argon atmosphere. TMS-N3 (1.6 ml) and tin (IV) chloride (0.2 ml) was then added to it and was allowed to stir for additional 15 h at room temperature (28° C.). After the mentioned time, reaction mixture was diluted with DCM and saturated with sodium bicarbonate solution to quench excess of tin(IV) chloride and stirred vigorously for 30 min. The mixture was then poured in water and the product was extracted with DCM, dried over sodium sulfate and was used without any further purification. Yield: 92%. $^1$H NMR (200 MHz, CDCl$_3$): δ in ppm 5.24 (apt t, 2H), 4.95 (t, 1H), 4.72 (d, 1H), 4.13 (d, 1H), 3.77 (s, 3H), 2.07 (s, 3H), 2.03 (s, 3H), 2.01 (s, 3H). LC-MS/MS (in MeCN) m/z calculated–359.29; observed [M+Na]–382.35. FTIR (cm$^{-1}$): 2121 (N3).

Example 4: Synthesis of 4-(Trimethylsilane)ethynylstyrene (4) from 4-bromostyrene To 1.86 gm of 4-bromostyrene, 2.28 gm of ethynyltrimethylsilane, 30 mg of copper (I) iodide was added 40 ml dry Et$_3$N. The reaction mixture was heated at 50° C. After 5 min, 150 mg of bis(triphenylphosphine) palladium (II) dichloride was added to the above mixture and allowed to stir for 16 h at the same temperature. Afterwards trimethylamine salt was filtered off followed by distillation under vacuum. The crude product was column purified using pet ether. Yield: 59%. $^1$H NMR (200 MHz, CDCl$_3$): δ in ppm 7.21 (d, o-Ar, 2H), 7.16 (d, m-Ar, 2H), 6.48 (dd, 1H), 5.61 (d, 1H), 5.12 (d, 1H), 0.28 (s, Si(Me)3), 9H). FTIR (cm$^{-1}$): 2157 (triple bond C—Si).

Example 5: Synthesis of 4-ethynylstyrene (5)

The silyl protected styrene (1 g) was dissolved in 5 ml dry THF and to it 1.0 M solution of tetra-n-butyl ammonium fluoride (7.5 ml) was added drop-wise. The reaction mixture was stirred at room temperature (28° C.) for one hour and then THF was evaporated under vacuum. The crude product was partitioned in DCM and water and the water layer was extracted twice with DCM and the combined layer was evaporated to dryness. The product was column purified using pet ether. Yield: 90%. $^1$H NMR (200 MHz, CDCl$_3$): δ in ppm 7.36 (o-Ar, 2H), 7.31 (d, m-Ar, 2H), 6.64 (dd, 1H), 5.75 (d, 1H), 5.26 (d, 1H), 3.04 (s, 1H). FTIR (cm$^{-1}$): 3295 (free Alkyne C—).

Example 6: Click Reaction to Synthesize (6)

In two neck round bottom flask was added 1 gm of 4-ethynylstyrene (5) and 2.4 g of 2, 3, 4-tri-O-acetyl-1-azido-1-deoxy-β-D-glucuronic acid methyl ester (3) in dry THF and the mixture was subjected to three freeze/thaw cycle. Then 480 mg of copper sulfate and 620 mg of sodium ascorbate in minimum quantity of water was added to the mixture. The mixture was allowed to stir for 24 h under argon atmosphere. The progress of reaction was monitored using FTIR analysis. Once FTIR showed complete absence of free alkyne C—H peak, the reaction was stopped and the reaction mixture was subjected to dryness under vacuum. The product was purified using pet ether/ethyl acetate (40/60) to afford (2R, 3S, 4R, 5S, 6R)-2-(methoxycarbonyl)-6-(4-(4-vinylphenyl)-1H-1,2,3-triazol-1-yl)tetrahydro-2H-pyran-3,4,5-triyl triacetate. Yield: 80%. $^1$H NMR (200 MHz, CDCl3): δ in ppm 8.06 (s, 1H), 7.79 (d, 2H), 7.51 (d, 2H), 6.73 (q, 1H), 6.01 (d, 1H), 5.85 (d, 1H), 5.51-5.33 (m, 4H), 4.37 (d, 1H), 3.77 (s, 3H), 2.09 (s, 6H), 1.90 (s, 3H). LC-MS/MS (in AcCN) m/z calculated–487.16; observed [M+H]–488.16, [M+Na]–510.15, [M+K]–526.12.

Example 7: Polymerization to Synthesize PS-PGlu (7)

(2R, 3S, 4R, 5S, 6R)-2-(methoxycarbonyl)-6-(4-(4-vinylphenyl)-1H-1,2,3-triazol-1-yl)tetrahydro-2H-pyran-3,4,5-triyl triacetate (1 gm), AIBN (50 mg) were taken together in a schlenk tube. To it 10 ml dry DMF was added. This mixture was degassed using three freeze/thaw cycle. The schlenk tube was then placed in oil bath at 80° C. for 24 h while stirring at 750 rpm. After 24 h, the reaction mixture was cooled and further diluted with minimum amount of THF. The polymer was then precipitated by pouring the solution in excess methanol and oligomers were removed by repeating three precipitation/filtration cycles. Yield: 55%. $^1$H NMR (400 MHz, CDCl$_3$): δ in ppm 8.45 (t, 1H), 7.42 (b, 2H), 6.61 (b, 2H), 6.30 (b, 1H), 5.62 (m, 3H), 4.55 (m, 1H), 3.72 (s, 6H), 2.09 (s, 6H), 1.88 (s, 3H), 1.69 (s. 3H).

Example 8: Deprotection of Protected Glucuronic Acid Bearing Polystyrene Polymer (PS-PGlu) to Obtain PS-DGlu (8)

100 mg of the polymer was dissolved in 5 ml dichloromethane and 2 ml methanol mixture. To it 0.7 ml 25 weight % sodium methoxide in methanol was added. This mixture was allowed to stir for 8 h. After rotary evaporation, polymer was washed with acetone and dissolve in 1:1 THF:water mixture. Then dilute HCl (0.025 M) was added and the reaction was stirred for additional 12 h. Then the excess solvent was removed and polymer was dissolved in minimum amount of water followed by dialyzing it against deionized water using 1 kD molecular weight cutoff dialysis membrane for 3 days, changing water thrice. Final polymer PS-DGlu was obtained as white powder after freeze drying the dialyzed solution. FTIR (cm$^{-1}$):3354 (broad peak), 1727, 1611, 1411, 1335, 1100, 1024, 818, 687.

Example 9: Preparation of PSG-OPV-n Using PS-DGlu (8) as Surfactant

The PS-DGlu polymer was used as a surfactant in the mini-emulsion polymerization process for synthesizing novel glucuronic acid functionalized polystyrene nanobead covalently incorporating (oligo) p-phenylenevinylene (OPV) nanosensor (PSG-OPV-n). The organic phase consisted of styrene (1 g), HD (48 mg), and polymerizable OPV dye (30 mg), while the aqueous phase consisted of water (4 g), initiator (ACVA) (16 mg), and a varying amount of PS-DGlu polymer (values are mentioned in Table 1). The organic phase was then added dropwise to the aqueous phase and kept for pre-emulsification at room temperature (28° C.) for another 1 h, followed by sonication under an ice cooled condition for 20 min. The mini-emulsion was then allowed to polymerize at 70° C. for 20 h with a stirring speed of 750 rpm. After quenching the polymerization with two drops of 1 wt % hydroquinone, the obtained latex was purified by dialysis using a 6 kDa MW cutoff membrane for 3 days.

Example 10: Calculation of Dye Loading Content (DLC)

3 mg of dried polymer (PSG-OPV-n) was taken in 3 mL of THF and its absorbance was recorded using absorption spectroscopy. This absorbance was used to calculate the dye loading from the molar absorptivity of OPV in THF (40,360 Lmol$^{-1}$ cm$^{-1}$) at its absorption maxima.

Example 11: Sensing of Free Bilirubin in Aqueous Medium Using PSG-OPV-n

The stock solution of polymer (PSG-OPV-n) was prepared at a concentration of 0.1 mg/3 mL in ches buffer at pH 10. Varying concentration of bilirubin solution ranging from $1 \times 10^{-6}$ to $5 \times 10^{-5}$ M in ches buffer at pH=10 were prepared and kept in dark. All the solutions were kept in dark at 18° C. The change in emission and absorption intensity of polymer after the addition of different concentrations of bilirubin were recorded at 18° C. with slit width of 1 nm. Efficient FRET (fluorescence resonance energy transfer) is carried out from OPV polymer to bilirubin leading to spectral overlap between emission of OPV and absorption of bilirubin resulting in the quenching of emission of the polystyrene with simultaneous weak emission from bilirubin.

Mechanism of Sensing

In order to examine the possibility for existence of different sensing mechanisms for the quenching of OPV emission upon interaction with bilirubin, emission quenching of OPV was further analyzed using Stern-Volmer equation to establish the relation between emission intensity of OPV with respect to concentration of bilirubin. Inset showed linear range of Io/Ivs bilirubin concentration from $1 \times 10^{-7}$ M to $1 \times 10^{-5}$ M. Thus, only one prominent mechanism was involved up to $1 \times 10^{-5}$M bilirubin concentration. It was the highest quenching constant value among other reported bilirubin sensors in literature (FIG. 13).

The selectivity of PSG-OPV-5 was checked from among the library of other additives such as NaCl, KCl, glucose, sucrose and cholesterol using same concentration of polymer (0.1 mg/3 mL) which was added the fixed concentration of each of the analytes ($3 \times 10^{-5}$M) and their emission spectra was observed. No appreciable quenching was observed upon addition of analytes at concentration of $3\times10^{-5}$ M other than bilirubin which exhibited almost 97% quenching at same concentration. This together with high quenching constant value signified the high selectivity of polymer towards bilirubin.

Example 12: Sensing of Free Bilirubin in Human Serum Using PSG-OPV-n

Fixed amount of human blood serum (100 μL) was added to varying concentration of bilirubin in the range of $1\times10^{-6}$ M to $3\times10^{-5}$ M. These solutions were then added to fixed concentration of polymer (0.1 mg/3 mL) in ches buffer at pH=10 to make the final volume of 3 mL. The change in emission and absorption intensity of polymer after the addition of different concentrations of bilirubin were recorded at 18° C. with slit width of 1 nm. One separate experiment was conducted using same volume (3 mL) of polymer and serum without adding bilirubin at pH=10.

Example 13: The Detection of Bilirubin Using PSG-OPV-n by Using Kit

A is polymer stock solution (0.1 mg/mL) to which can be added blood sample of patient with help of dropper B. The solution can be poured to Analysis chamber C which is equipped with UV chamber D at the bottom. If blue emission of the polymer turns cyan then free bilirubin is present in the blood sample.

Advantages of the Invention

1) Development of new water soluble, polymer surfactant (PS-DGlu) with high molecular weight, good photostability in water dispersion and exceptionally good stability in physiological medium.
2) Successful use of prepared polymer surfactant PS-DGlu for making polystyrene incorporated OPV beads (PSG-OPV) with size in nanometer range.
3) Appreciably high quantum yield and good photostability of nanoparticle dispersion (PSG-OPV) in water along with good stability in physiological environment.
4) Commercial polymers such as polystyrene (PS) are relatively low cost and are produced in large quantities. Sensor substrates are for quick and accurate estimation of free bilirubin. These polymeric nanobeads are developed using water soluble polymeric surfactant.
5) The present invention provides a simple, fast, easy synthesis of polymer via mini-emulsion polymerization and for developing a kit for detection of bilirubin in human serum.
6) In present invention, OPV not only serves as a crosslinker but also as a FRET pair with bilirubin.
7) Glucuronic acid not only provides water solubility to the polystyrene polymer but also provides selective interaction with the bilirubin.
8) The present invention possesses good stability in physiological environment and provides a trigger free emission of fluorescent nanoparticle.

We claim:
1. A water soluble polymer surfactant (PS-DGlu) of formula (I) comprising a hydrophobic polystyrene and a hydrophilic glucuronic acid units joined together with a triazole moiety;

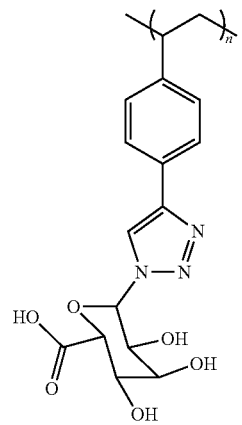

Formula (I)

wherein n is 30-50.

2. A process for the preparation of the water soluble polymer surfactant of claim 1, comprising the steps of:
a) adding an iodine solution to a mixture of D-glucuronic acid and acetic anhydride at a temperature in the range of 0° C. to −5° C. to obtain a reaction mixture; stirring the mixture at a temperature in the range of 0° C. to −5° C. for a time period ranging from 2 to 3 hours, followed by stirring at a temperature in the range of 25° C. to 30° C. for a time period ranging from 2.5 to 4 hours to obtain penta-acetate glucuronic acid (1)

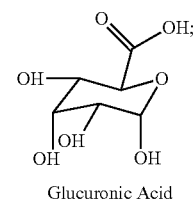

Glucuronic Acid b) refluxing the penta-acetate glucuronic acid (1) as obtained in step (a) in dry methanol at a temperature in the range of 60° C. to 90° C. for a time period ranging from 12 to 26 hours to obtain 1, 2, 3, 4-Tetra-O-acetyl-methyl-β-D-glucuronide (2)

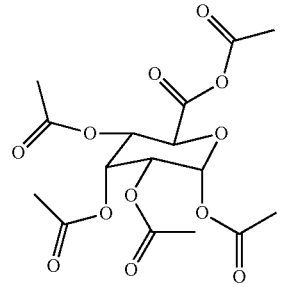

(1)

(2)

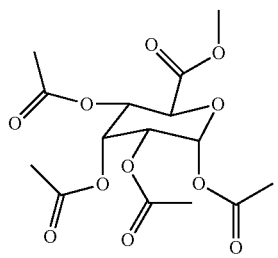

c) adding TMS-azide and tin (IV) chloride to the 1, 2, 3, 4-Tetra-O-Acetyl-methyl-β-D-Glucuronide (2) as obtained in step (b) in a first solvent, followed by stirring at a temperature in the range of 25 to 30° C. for a time period ranging from 15 to 20 hours to obtain 2, 3, 4-tri-O-acetyl-1-azido-1-deoxy-β-D-glucuronic acid methyl ester (3)

(3)

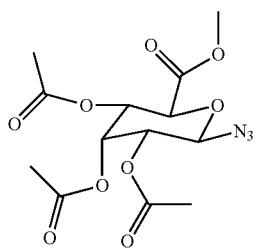

d) heating a reaction mixture of 4-bromostyrene, ethynyltrimethylsilane, copper(I) iodide and triethyl amine at a temperature in the range of 50 to 60° C. for a time period ranging from 5 to 15 minutes, followed by adding bis(triphenylphosphine) palladium (II) dichloride followed by stirring at a temperature in the range of 50 to 60° C. for a time period ranging from 16 to 17 hours to obtain 4-(trimethylsilane)ethynylstyrene (4)

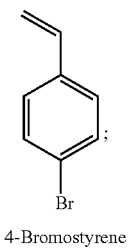

4-Bromostyrene (4)

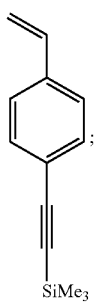

e) adding tetra-n-butyl ammonium fluoride to the 4-(Trimethylsilane)ethynylstyrene (4) as obtained in step (d) in a second solvent to obtain a reaction mixture, followed by stirring the reaction mixture at a temperature in the range of 25 to 30° C. for a time period ranging from 1 to 2 hours to obtain 4-ethynylstyrene (5)

(5)

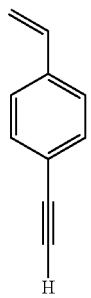

f) adding a copper sulfate and sodium ascorbate in a water to the 4-ethynylstyrene (5) as obtained in step (e) and the 2, 3, 4-tri-O-acetyl-1-azido-1-deoxy-β-D-glucuronic acid methyl ester (3) as obtained in step (c) in a third solvent to obtain a reaction mixture; stirring the reaction mixture at a temperature in the range of 25° C. to 30° C. for a time period ranging from 24 to 25 hours to obtain (2R, 3S, 4R, 5S, 6R)-2-(methoxycarbonyl)-6-(4-(4-vinylphenyl)-1H-1,2,3-triazol-1-yl)tetrahydro-2H-pyran-3,4,5-triyl triacetate (6)

(6)

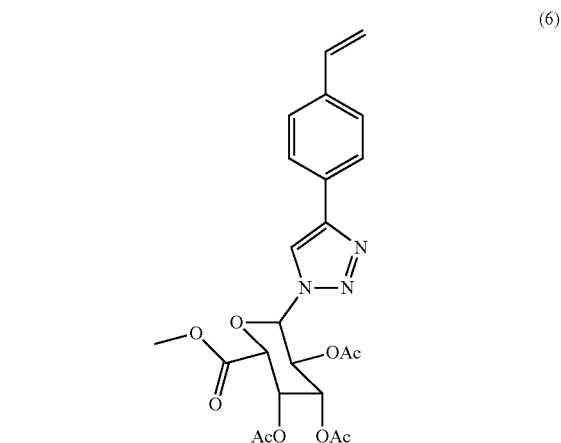 [SMILES: C=Cc1ccc(-c2cn(C3OC(C(=O)OC)C(OC(C)=O)C(OC(C)=O)C3OC(C)=O)nn2)cc1]

g) heating a mixture of (2R, 3S, 4R, 5S, 6R)-2-(methoxycarbonyl)-6-(4-(4-vinylphenyl)-1H-1,2,3-triazol-1-yl) tetrahydro-2H-pyran-3,4,5-triyl triacetate (6) as obtained in step (f), AIBN and a fourth solvent at a temperature in the range of 80° C. to 90° C. for a time period ranging from 24 to 25 hours to obtain a protected polymer (7)

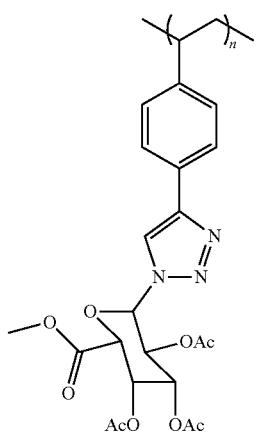

(7)

h) adding sodium methoxide in a fifth solvent into the protected polymer (7) as obtained in step (g) in a solvent followed by stirring and refluxing for a time period ranging from 8 to 10 hours to obtain a polymer; and i) dissolving the polymer as obtained in step (h), in a sixth solvent followed by adding hydrochloric acid and stirring at a temperature in the range of 25 to 30° C. for a time period ranging from 24 to 25 hours to obtain the water soluble polymer surfactant of claim 1.

3. The process according to claim 2, wherein the one or more of the first solvent, the second solvent, the third solvent, the fourth solvent, the fifth solvent, and the sixth solvent are selected from the group consisting of methanol, dichloromethane, tetrahydrofuran, dimethylformamide, water or a combination thereof.

4. A mini-emulsion polymerization process using a water soluble polymer surfactant, comprising the steps of:
   a) preparing an organic phase comprising a styrene, a co-stabilizer and a polymerizable (oligo) p-phenylenevinylene (OPV) dye;
   b) preparing an aqueous phase comprising an initiator and the water soluble polymer surfactant of claim 1 in a water;
   c) adding the organic phase as obtained in step (a) drop-wise to the aqueous phase as obtained in step (b) and pre-emulsifying at a temperature in the range of 21° C. to 25° C. followed by sonication under ice cooled condition to obtain a mini-emulsion;
   d) polymerizing the mini-emulsion as obtained in step (c) at a temperature of 70° C. for 20 hours with a stirring at a speed of 750 rpm to obtain a polymerized mini-emulsion;
   e) quenching the polymerized mini-emulsion of step (d) to obtain a latex; and
   f) purifying the latex as obtained in step (e), to obtain a glucuronic acid functionalized polystyrene nanobead covalently incorporating (oligo) p-phenylenevinylene (OPV) nanosensor (PSG-OPV-n) bead.

5. The process according to claim 4, wherein the quenching is achieved by adding two drops of 1 wt % hydroquinone.

6. The process according to claim 4, wherein the latex is purified by dialysis using a 6 kD MW cut-off membrane for three days.

7. The process according to claim 4, wherein the co-stabilizer is selected from the group consisting of hexadecane, cetyl alcohol, dodecyl methacrylate and stearyl methacrylate.

8. The process according to claim 4, wherein the initiator is selected from the group consisting of 4,4'-Azobis(4-cyanovaleric acid) (ACVA), azobisisobutyronitrile (AIBN), potassium peroxydisulfate (KPS), lactoperoxidase (LPO) and benzoyl peroxide (BPO).

9. The process according to claim 4, wherein the weight/weight (w/w) ratio of the water soluble polymer surfactant to (oligo) p-phenylenevinylene (OPV) dye is 1:3 to 5:3 in the glucuronic acid functionalized polystyrene nanobead covalently incorporating (oligo) p-phenylenevinylene (OPV) nanosensor (PSG-OPV-n) bead.

10. The process according to claim 4, wherein a size of the glucuronic acid functionalized polystyrene nanobead covalently incorporating (oligo) p-phenylenevinylene (OPV) nanosensor (PSG-OPV-n) bead is in the range of 163 to 328 nm.

11. A method of detection of bilirubin, comprising the steps of:
   a) preparing a sample solution in a water or a buffer at pH=10 by the addition of NaOH;
   b) titrating the glucuronic acid functionalized polystyrene nanobead covalently incorporating (oligo) p-phenylenevinylene (OPV) nanosensor (PSG-OPV-n) bead as obtained in claim 4 in a distilled water or a buffer with the sample solution of step (a); and
   c) determining, by fluorimetry, a quenching of fluorescence intensity at 446 nm λmax, confirming the presence of bilirubin.

12. A kit for the detection of bilirubin, comprising:
   a) a stock solution of the glucuronic acid functionalized polystyrene nanobead covalently incorporating (oligo) p-phenylenevinylene (OPV) nanosensor (PSG-OPV-n) bead as obtained in claim 4;
   b) a graduated dropper;
   c) an analysis chamber; and
   d) a UV chamber.

13. A method of detection of bilirubin in a sample, comprising the steps of:
   a) adding a sample into a stock solution of the glucuronic acid functionalized polystyrene nanobead covalently incorporating (oligo) p-phenylenevinylene (OPV) nanosensor (PSG-OPV-n) bead as obtained in claim 4 with the help of a dropper to obtain a sample solution;
   b) pouring the sample solution of step (a) into an analysis chamber equipped with an UV chamber at the bottom; and
   c) detecting a change in blue emission of the sample solution of step (b), confirming the presence of bilirubin in the sample.

14. The method according to claim 13, wherein the change in blue emission of the sample solution is visually detectable as a cyan color.

* * * * *